United States Patent
Ng et al.

(10) Patent No.: US 10,316,265 B2
(45) Date of Patent: Jun. 11, 2019

(54) LOW VISCOSITY LOW VOLATILITY LUBRICATING OIL BASE STOCKS AND METHODS OF USE THEREOF

(71) Applicant: ExxonMobil Research and Engineering Company, Annandale, NJ (US)

(72) Inventors: Man Kit Ng, Basking Ridge, NJ (US); Halou Oumar-Mahamat, Belle Mead, NJ (US); Hong Cheng, Bridgewater, NJ (US); David A. Blain, Cherry Hill, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 98 days.

(21) Appl. No.: 15/384,396

(22) Filed: Dec. 20, 2016

(65) Prior Publication Data

US 2017/0183597 A1    Jun. 29, 2017

Related U.S. Application Data

(60) Provisional application No. 62/271,567, filed on Dec. 28, 2015.

(51) Int. Cl.
*C10M 129/72* (2006.01)
*C07C 69/34* (2006.01)
(Continued)

(52) U.S. Cl.
CPC .......... *C10M 129/72* (2013.01); *C07C 69/34* (2013.01); *C10M 105/36* (2013.01);
(Continued)

(58) Field of Classification Search
CPC .......... C10M 129/72; C10M 2207/282; C10M 2203/024; C10N 2240/04; C10N 2240/10;
(Continued)

(56) References Cited

U.S. PATENT DOCUMENTS

| | | | |
|---|---|---|---|
| 2,417,281 | A | 3/1947 | Wasson et al. |
| 2,757,139 | A | 7/1956 | Matuszak et al. |

(Continued)

FOREIGN PATENT DOCUMENTS

| | | |
|---|---|---|
| DE | 3521711 A1 | 12/1986 |
| EP | 1040115 B1 | 6/2004 |

(Continued)

OTHER PUBLICATIONS

Dufek, Edward et al. (Esters of mono-, di-, and tricarboxystearic acid as lubricants), Journal of the American Oil Chemists' Society (1974), 51(8), 351-355 (Year: 1974).*

(Continued)

*Primary Examiner* — Taiwo Oladapo
(74) *Attorney, Agent, or Firm* — Robert A. Migliorini

(57) ABSTRACT

A composition including one or more diester compounds represented by the formula as defined herein. The composition has a viscosity ($Kv_{100}$) from about 1 cSt to about 10 cSt at 100° C. as determined by ASTM D445, a viscosity index (VI) from about −100 to about 300 as determined by ASTM D2270, and a Noack volatility of no greater than 50 percent as determined by ASTM D5800. A process for producing the composition, a lubricating oil base stock and lubricating oil containing the composition, and a method for improving one or more of thermal and oxidative stability, solubility and dispersancy of polar additives, deposit control and traction control in a lubricating oil by using as the lubricating oil a formulated oil containing the composition.

28 Claims, 5 Drawing Sheets

| Entry | Source | Basestock | ASTM D445 or ASTM D7042 Kinematic Viscosity (@100 °C), cSt | ASTM D445 or ASTM D7042 Kinematic Viscosity (@40 °C), cSt | ASTM D2700 Viscosity Index (VI) | ASTM D5800 Noack (%) |
|---|---|---|---|---|---|---|
| 1 | Example 1 | Dihexyl 2-octylsuccinate | 2.5 | 8.7 | 110 | 24 |
| 2 | Example 2 | Diheptyl 2-octylsuccinate | 2.8 | 10.3 | 119 | 14 |
| 3 | Example 3 | Dipentyl 2-dodecylsuccinate | 3.0 | 10.9 | 127 | 13 |
| 4 | Commercial | 2-Ethylhexyl oleate | 2.8 | 8.0 | 238 | 22 |
| 5 | Commercial | Bis(2-ethylhexyl) adipate | 2.3 | 7.7 | 116 | 41 |
| 6 | Commercial | Diisononyl adipate | 3.1 | 10.8 | 150 | 17 |
| 7 | Commercial | Diisodecyl adipate | 3.6 | 14.1 | 146 | 14 |
| 8 | Commercial | Bis(2-ethylhexyl) sebacate | 3.2 | 11.6 | 152 | 16 |
| 9 | Commercial | Di-2-ethylhexyl azelate | 3.0 | 10.7 | 137 | 29 |
| 10 | Commercial | Bis(2-ethylhexyl) dodecanedioate | 3.8 | 14.1 | 165 | 11 |
| 11 | Commercial | Esterex™ A32 | 2.8 | 9.5 | 149 | 30 |
| 12 | Commercial | Esterex™ A34 | 3.2 | 12.0 | 137 | 20 |
| 13 | Commercial | Esterex™ A41 | 3.6 | 14.0 | 144 | 16 |

(51) Int. Cl.
*C10M 105/36* (2006.01)
*C10M 111/02* (2006.01)

(52) U.S. Cl.
CPC ..... *C10M 111/02* (2013.01); *C10M 2203/024* (2013.01); *C10M 2207/282* (2013.01); *C10M 2207/2825* (2013.01); *C10M 2207/34* (2013.01); *C10M 2207/345* (2013.01); *C10N 2220/022* (2013.01); *C10N 2220/13* (2013.01); *C10N 2230/02* (2013.01); *C10N 2230/04* (2013.01); *C10N 2230/06* (2013.01); *C10N 2230/10* (2013.01); *C10N 2230/74* (2013.01); *C10N 2240/04* (2013.01); *C10N 2240/10* (2013.01)

(58) Field of Classification Search
CPC ............ C10N 2230/10; C10N 2230/04; C10N 2220/022; C10N 2230/74
See application file for complete search history.

(56) References Cited

U.S. PATENT DOCUMENTS

| | | | |
|---|---|---|---|
| 2,870,195 | A | 1/1959 | Heininger et al. |
| 2,936,856 | A | 5/1960 | Braunwarth et al. |
| 2,936,866 | A | 5/1960 | Kelly |
| 3,036,003 | A | 5/1962 | Verdol |
| 3,172,892 | A | 3/1965 | Le Suer et al. |
| 3,210,280 | A | 10/1965 | Rich, Jr. |
| 3,219,666 | A | 11/1965 | Norman et al. |
| 3,316,177 | A | 4/1967 | Dorer, Jr. |
| 3,345,327 | A | 10/1967 | Dexter et al. |
| 3,595,791 | A | 7/1971 | Cohen |
| 3,984,460 | A | 10/1976 | Spivack |
| 4,234,435 | A | 11/1980 | Meinhardt et al. |
| 4,827,064 | A | 5/1989 | Wu |
| 4,827,073 | A | 5/1989 | Wu |
| 4,889,647 | A | 12/1989 | Rowan et al. |
| 4,956,122 | A | 9/1990 | Watts et al. |
| 4,976,464 | A | 12/1990 | Coyle et al. |
| 5,273,672 | A * | 12/1993 | Dasai ............... C10M 129/00 252/79 |
| 5,488,121 | A | 1/1996 | O'Lenick, Jr. |
| 5,639,791 | A | 6/1997 | O'Lenick, Jr. |
| 5,705,458 | A | 1/1998 | Roby et al. |
| 5,759,968 | A | 6/1998 | Furutani et al. |
| 6,008,167 | A | 12/1999 | Appleman et al. |
| 6,034,039 | A | 3/2000 | Gomes et al. |
| 6,346,504 | B1 | 2/2002 | Appelman et al. |
| 6,642,188 | B1 * | 11/2003 | Hartley ............... C10M 167/00 508/291 |
| 7,008,909 | B2 | 3/2006 | Burgo et al. |
| 8,343,899 | B2 | 1/2013 | Ichisaka et al. |
| 8,673,831 | B2 | 3/2014 | Kitching et al. |
| 2004/0072703 | A1 | 4/2004 | Burgo et al. |
| 2005/0014961 | A1 | 1/2005 | Walele et al. |
| 2005/0048091 | A1 | 3/2005 | Raney et al. |
| 2005/0059563 | A1 | 3/2005 | Sullivan et al. |
| 2007/0172437 | A1 | 7/2007 | Bertz et al. |
| 2009/0036333 | A1 | 2/2009 | Scholier et al. |
| 2010/0261628 | A1 | 10/2010 | Scherer et al. |
| 2011/0039740 | A1 | 2/2011 | Kitching et al. |
| 2013/0090273 | A1 | 4/2013 | Martin et al. |
| 2013/0090276 | A1 | 4/2013 | Jung et al. |
| 2013/0096042 | A1 | 4/2013 | Oda |
| 2014/0121143 | A1 | 5/2014 | Patil et al. |
| 2015/0166912 | A1 | 6/2015 | Sharko et al. |

FOREIGN PATENT DOCUMENTS

| | | | |
|---|---|---|---|
| EP | 2157159 A1 | 2/2010 | |
| EP | 2302022 A1 | 3/2011 | |
| GB | 1059296 A | 12/1967 | |
| GB | 1099716 A | 1/1968 | |
| GB | 1099716 A * | 1/1968 | ............. C10M 3/00 |
| JP | 63066293 | 3/1988 | |
| JP | 5159159 B2 | 11/2008 | |
| JP | 5334421 B2 | 11/2013 | |
| JP | 5334425 B2 | 11/2013 | |
| JP | 2014139306 A | 7/2014 | |
| WO | 99/31113 A1 | 6/1999 | |
| WO | 200157099 A1 | 8/2001 | |
| WO | 2008061709 A1 | 5/2008 | |
| WO | 2009130445 A1 | 10/2009 | |
| WO | 2003095407 A2 | 11/2011 | |
| WO | 2015040937 A1 | 3/2015 | |

OTHER PUBLICATIONS

Eastwood, J, "Esters The most Versatile of Base Stock Technologies", Lube-Tech, Lube Magazine, No. 129, Oct. 2015.

Baek, Seung-Yeob, et al. "Synthesis of Succinic Acid Alkyl Half-Ester Derivatives with Improved Lubricity Characteristics", Industrial & Engineering Chemistry Research, ACS Publications, American Chemical Society, vol. 51, No. 9, 2012.

Tabenkin B. et al. "Evaluation of Esters of phenylacetic Acid as Precursors of Penicillin G", Archives of Biochemistry, Academic press, US, vol. 38, Jan. 1952.

The International Search Report and Written Opinion of PCT/US2016/067962 dated Jul. 28, 2017.

The International Search Report and Written Opinion of PCT/US2016/067964 dated May 9, 2017.

The International Search Report and Written Opinion of PCT/US2016/067975 dated Jul. 28, 2017.

The International Search Report and Written Opinion of PCT/US2016/067986 dated May 3, 2017.

* cited by examiner

Fig. 1

| Entry | Source | Basestock | ASTM D445 or ASTM D7042 Kinematic Viscosity (@100 °C), cSt | ASTM D445 or ASTM D7042 Kinematic Viscosity (@40 °C), cSt | ASTM D2700 Viscosity Index (VI) | ASTM D5800 Noack (%) |
|---|---|---|---|---|---|---|
| 1 | Example 1 | Dihexyl 2-octylsuccinate | 2.5 | 8.7 | 110 | 24 |
| 2 | Example 2 | Diheptyl 2-octylsuccinate | 2.8 | 10.3 | 119 | 14 |
| 3 | Example 3 | Dipentyl 2-dodecylsuccinate | 3.0 | 10.9 | 127 | 13 |
| 4 | Commercial | 2-Ethylhexyl oleate | 2.8 | 8.0 | 238 | 22 |
| 5 | Commercial | Bis(2-ethylhexyl) adipate | 2.3 | 7.7 | 116 | 41 |
| 6 | Commercial | Diisononyl adipate | 3.1 | 10.8 | 150 | 17 |
| 7 | Commercial | Diisodecyl adipate | 3.6 | 14.1 | 146 | 14 |
| 8 | Commercial | Bis(2-ethylhexyl) sebacate | 3.2 | 11.6 | 152 | 16 |
| 9 | Commercial | Di-2-ethylhexyl azelate | 3.0 | 10.7 | 137 | 29 |
| 10 | Commercial | Bis(2-ethylhexyl) dodecanedioate | 3.8 | 14.1 | 165 | 11 |
| 11 | Commercial | Esterex™ A32 | 2.8 | 9.5 | 149 | 30 |
| 12 | Commercial | Esterex™ A34 | 3.2 | 12.0 | 137 | 20 |
| 13 | Commercial | Esterex™ A41 | 3.6 | 14.0 | 144 | 16 |

| Entry | Source | Formulation based on basestock | ASTM D4683 HTHS (cP, 150 °C) | ASTM D5800 Noack (%) | Average Traction Coefficient | Traction Improvement over Commercial Ester |
|---|---|---|---|---|---|---|
| 1 | Example 1 | Dihexyl 2-octylsuccinate | 1.46 | 19.0 | 0.00706 | 29.25% |
| 2 | Example 2 | Diheptyl 2-octylsuccinate | 1.68 | 11.7 | 0.00658 | 34.11% |
| 3 | Commercial | Diisooctyl adipate | 1.72 | 22.3 | 0.00999 | Reference |
| 4 | Commercial | nC7 Trimethylolpropane ester | Not Applicable - Low additive compatibility | | | |
| 5 | Commercial | nC7 Trimethylolpropane ester/SpectraSyn 4/QHVI3™ (2/1/1 wt. mixture) | 1.78 | 16.6 | - | - |
| 6 | Commercial | SpectraSyn 4 | 1.97 | 8.6 | 0.00929 | 6.97% |

| Entry | Source | Engine Oil Formulation based on basestock | Catalytic Oxidation Test at 163°C & 120 hours — Change in Kinematic Viscosity at 100°C ($\Delta Kv_{100}$), % | 210 Hour Oxidation Stability Test at 165°C — Time to 200% Increase of Kinematic Viscosity at 40°C ($Kv_{40}$), hours |
|---|---|---|---|---|
| 1 | Example 2 | Diheptyl 2-octylsuccinate | 9.4 | >210 |
| 2 | Commercial | Diisooctyl adipate | 34.5 | 97 |
| 3 | Commercial | SpectraSyn 4 | 7.2 | 89 |

LOW VISCOSITY LOW VOLATILITY LUBRICATING OIL BASE STOCKS AND METHODS OF USE THEREOF

CROSS-REFERENCE TO RELATED APPLICATIONS

This application claims priority to U.S. Provisional Application Ser. No. 62/271,567 filed Dec. 28, 2015, which is herein incorporated by reference in its entirety. This application is related to three (3) other co-pending U.S. applications, filed on even date herewith, and identified by the following numbers and titles: Ser. No. 15/384,471 entitled "Low Viscosity Low Volatility Lubricating Oil Base Stocks and Methods of Use Thereof"; Ser. No. 15/384,421 entitled "Low Viscosity Low Volatility Lubricating Oil Base Stocks and Methods of Use Thereof" and Ser. No. 15/384,443 entitled "High Viscosity Index Monomethyl Ester Lubricating Oil Base Stocks and Methods of Making and Use Thereof", which are all incorporated herein by reference in their entirety.

FIELD

This disclosure relates to low viscosity, low volatility compositions that include one or more diesters, a process for producing the compositions, a lubricating oil base stock and lubricating oil containing the composition, and a method for improving one or more of thermal and oxidative stability, solubility and dispersancy of polar additives, deposit control and traction control in a lubricating oil by using as the lubricating oil a formulated oil containing the composition.

BACKGROUND

Lubricants in commercial use today are prepared from a variety of natural and synthetic base stocks admixed with various additive packages and solvents depending upon their intended application. The base stocks typically include mineral oils, polyalphaolefins (PAO), gas-to-liquid base oils (GTL), silicone oils, phosphate esters, diesters, polyol esters, and the like.

A major trend for passenger car engine oils (PCEOs) is an overall improvement in quality as higher quality base stocks become more readily available. Typically the highest quality PCEO products are formulated with base stocks such as PAOs or GTL stocks admixed with various additive packages.

For improving fuel economy, base oil viscosity is very important. Substantial improved fuel economy (>2%) requires breakthroughs in: (1) base oil volatility (2) durability and (3) friction. Friction losses occur between the moving components within the engine. Models developed to date indicate that fuel economy is heavily influenced by the lubricant properties at high shear. The base stock contributes a greater proportion of the total viscosity under high shear conditions than under low shear. Lowering base stock viscosity is likely to have the largest impact on future fuel economy gains.

Current commercial PAO fluids (e.g., SpectraSyn™ 2) based on hydrocarbon and commercial esters (e.g., 2-ethylhexyl adipate, di-2-ethylhexyl azelate, Esterex™ A32, Esterex™ A34) do not adequately allow formulation of ultra-low viscosity lubricant while still meeting API specification (e.g., Noack volatility of 15% or less). In order to formulate ultra-low viscosity lubricant for fuel economy benefit, it is desirable to have low viscosity and low volatility properties co-exist in the same base stock, for meeting volatility requirement. In addition, the base stock should also possess adequate thermal and oxidative stability at high temperature to prevent or minimize deposit formation. Good compatibility with additives commonly used in lubricant formulations (passenger vehicle lubricants (PVL), commercial vehicle lubricants (CVL) and, industrial lubricants), good low temperature properties, and acceptable viscosity indices are also necessary for the base stocks.

Poly-α-olefins (PAOs) are important lube base stocks with many excellent lubricant properties, including high viscosity index (VI), low volatility and are available in various viscosity range ($Kv_{100}$ 2-1000 cSt). However, PAOs are paraffinic hydrocarbons with low polarity. This low polarity leads to low solubility and dispersancy for polar additives or sludge generated during service. To compensate for this low polarity, lube formulators usually add one or multiple polar cobase stocks. Ester or alkylated naphthalene (AN) is usually present at 1 wt. % to 50 wt. % levels in many finished lubricant formulations to increase the fluid polarity which improves the solubility of polar additives and sludge.

Therefore, there is a need for polar cobase fluids that provide appropriate solubility and dispersibility for polar additives or sludge generated during service of lubricating oils.

Future automotive and industrial trend suggest that there will be a need for advanced additive technology and synthetic base stocks with substantially better thermal and oxidative stability. This is primarily because of smaller sump sizes that will have more thermal and oxidative stresses on the lubricants. Performance requirements have become more stringent in the past 10 to 20 years and the demand for longer drain intervals has grown steadily. Also, the use of Group II, III, IV and V base oils is becoming more widespread. Such base oils have very little sulfur content since natural sulfur-containing antioxidants are either absent or removed during the severe refining process.

It is known that lubricant oils used in internal combustion engines and transmission of automobile engines or trucks are subjected to demanding environments during use. These environments result in the lubricant suffering oxidation catalyzed by the presence of impurities in the oil, such as iron (wear) compounds and elevated temperatures. The oxidation manifests itself by increase in acid or viscosity and deposit formation or any combination of these symptoms. These are controlled to some extent by the use of antioxidants which can extend the useful life of the lubricating oil, particularly by reducing or preventing unacceptable viscosity increases. Besides oxidation inhibition, other parameters such as rust and wear control are also important.

A major challenge in engine oil formulation is simultaneously achieving improved fuel economy while also achieving appropriate solubility and dispersibility for polar additives or sludge generated during service of lubricating oils and oxidative stability.

Therefore, there is need for better additive and base stock technology for lubricant compositions that will meet ever more stringent requirements of lubricant users. In particular, there is a need for advanced additive technology and synthetic base stocks with improved fuel economy, solubility and dispersibility for polar additives or sludge generated during service of lubricating oils, and oxidative stability.

The present disclosure also provides many additional advantages, which shall become apparent as described below.

SUMMARY

This disclosure provides compositions that include one or more diesters that have desirable low viscosity/low volatility properties while exhibiting good high-temperature thermal-oxidative stability. Thus, the lubricating oil base stocks of this disclosure provide a solution to achieve enhanced fuel economy and energy efficiency. In addition, good solvency for commonly used polar additives and potentially good hydrolytic, thermal and oxidative stability, deposit control and traction control are other advantages of these compositions.

This disclosure relates in part to a composition comprising one or more compounds represented by the formula

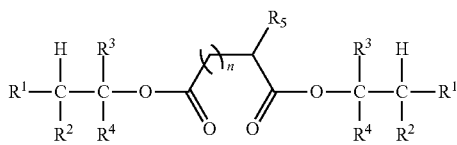

wherein each $R_1$ is independently a substituted or unsubstituted linear alkyl group ($C_1$-$C_{30}$), each $R_2$, $R_3$ and $R_4$ is hydrogen, $R_5$ is a substituted or unsubstituted alkyl group ($C_8$-$C_{30}$) or alkenyl group ($C_8$-$C_{30}$), and n is a value from about 0 to about 7. The composition has a viscosity ($Kv_{100}$) from about 1 cSt to about 10 cSt at 100° C. as determined by ASTM D445, a viscosity index (VI) from about −100 to about 300 as determined by ASTM D2270, and a Noack volatility of no greater than 50 percent as determined by ASTM D5800.

This disclosure also relates in part to a composition comprising one or more compounds represented by the formula

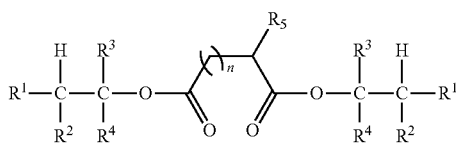

wherein each $R_1$ is independently a substituted or unsubstituted linear alkyl group ($C_1$-$C_{30}$), each $R_2$, $R_3$ and $R_4$ is hydrogen, $R_5$ is a substituted or unsubstituted alkyl group ($C_8$-$C_{30}$) or alkenyl group ($C_8$-$C_{30}$), and n is a value from about 0 to about 7. The composition has a viscosity ($Kv_{100}$) from about 1 cSt to about 10 cSt at 100° C. as determined by ASTM D445, a viscosity index (VI) from about −100 to about 300 as determined by ASTM D2270, and a Noack volatility of no greater than 50 percent as determined by ASTM D5800. The one or more compounds are produced by a process comprising reacting a substituted or unsubstituted alcohol having a hydrogen attached to a beta carbon thereof with a substituted or unsubstituted carboxylic diacid or anhydride, optionally in the presence of a catalyst and a solvent, under reaction conditions sufficient to produce said one or more compounds.

This disclosure further relates in part to a lubricating oil base stock comprising one or more compounds represented by the formula

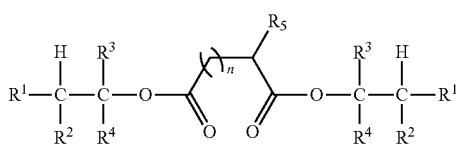

wherein each $R_1$ is independently a substituted or unsubstituted linear alkyl group ($C_1$-$C_{30}$), each $R_2$, $R_3$ and $R_4$ is hydrogen, $R_5$ is a substituted or unsubstituted alkyl group ($C_8$-$C_{30}$) or alkenyl group ($C_8$-$C_{30}$), and n is a value from about 0 to about 7. The composition has a viscosity ($Kv_{100}$) from about 1 cSt to about 10 cSt at 100° C. as determined by ASTM D445, a viscosity index (VI) from about −100 to about 300 as determined by ASTM D2270, and a Noack volatility of no greater than 50 percent as determined by ASTM D5800.

This disclosure yet further relates in part to a lubricating oil comprising a lubricating oil base stock component, and a diester cobase stock component; wherein said diester cobase stock comprises one or more compounds represented by the formula

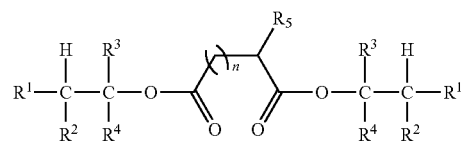

wherein each $R_1$ is independently a substituted or unsubstituted linear alkyl group ($C_1$-$C_{30}$), each $R_2$, $R_3$ and $R_4$ is hydrogen, $R_5$ is a substituted or unsubstituted alkyl group ($C_8$-$C_{30}$) or alkenyl group ($C_8$-$C_{30}$), and n is a value from about 0 to about 7. The composition has a viscosity ($Kv_{100}$) from about 1 cSt to about 10 cSt at 100° C. as determined by ASTM D445, a viscosity index (VI) from about −100 to about 300 as determined by ASTM D2270, and a Noack volatility of no greater than 50 percent as determined by ASTM D5800.

This disclosure also relates in part to a method for improving one or more of oxidative stability, solubility and dispersancy of polar additives of a lubricating oil by using as the lubricating oil a formulated oil comprising a lubricating oil base stock as a major component, and a diester cobase stock as a minor component; wherein said diester cobase stock comprises one or more compounds represented by the formula

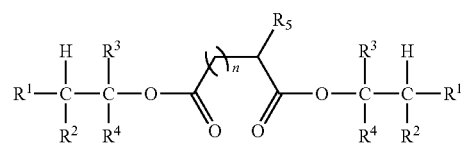

wherein each $R_1$ is independently a substituted or unsubstituted linear alkyl group ($C_1$-$C_{30}$), each $R_2$, $R_3$ and $R_4$ is hydrogen, $R_5$ is a substituted or unsubstituted alkyl group ($C_8$-$C_{30}$) or alkenyl group ($C_8$-$C_{30}$), and n is a value from about 0 to about 7. The composition has a viscosity ($Kv_{100}$) from about 1 cSt to about 10 cSt at 100° C. as determined by ASTM D445, a viscosity index (VI) from about −100 to about 300 as determined by ASTM D2270, and a Noack volatility of no greater than 50 percent as determined by ASTM D5800.

It has been surprisingly found that outstanding low viscosity low volatility properties, good high-temperature thermal and oxidative stability, good solvency for polar additives, deposit control, and traction benefits, can be attained in an engine lubricated with a lubricating oil by using as the lubricating oil a formulated oil in accordance with this disclosure. In particular, a lubricating oil base stock comprising one or more diesters exhibits low viscosity, low volatility, desired solvency for polar additives, superior oxidative stability, desired deposit control and traction benefits, which helps to prolong the useful life of lubricants and significantly improve the durability and resistance of lubricants when exposed to high temperatures.

The lubricating oils of this disclosure are particularly advantageous as passenger vehicle engine oil (PVEO) products, more specifically SAE 0WX, SAE SWX, or SAE 10WX, (where X=4, 8, 12, 16, 20, 30, 40, or 50), and similar oil formulations, especially oil formulations exhibiting lowered volatility when blended with the components of this invention. Furthermore, the esters of this invention can be used in low ash, low metals, low phosphorus oils, preferably formulated with ZDDP derived in part from secondary alcohols, with metallic detergents, such as salicylates, phenates and/or sulfonates, preferably magnesium and/or calcium, with succinimide dispersants or with boron-containing detergents or dispersants.

Further objects, features and advantages of the present disclosure will be understood by reference to the following drawings and detailed description.

BRIEF DESCRIPTION OF THE DRAWINGS

FIG. 1 shows lube properties including kinematic viscosities, viscosity indices (VI) and volatility of selected base stocks of this disclosure and commercially available ester base stocks in accordance with Example 4.

FIG. 3 shows high temperature high shear (HTHS) viscosity, Noack volatility, and traction results for low-viscosity engine oils formulated with base stocks of this disclosure and commercially available ester base stocks in accordance with Example 5.

FIG. 5 shows oxidative stability of engine oil formulated with a base stock of this disclosure and commercially available ester base stock and a Group IV PAO4 base stock.

DETAILED DESCRIPTION

Figure 2:
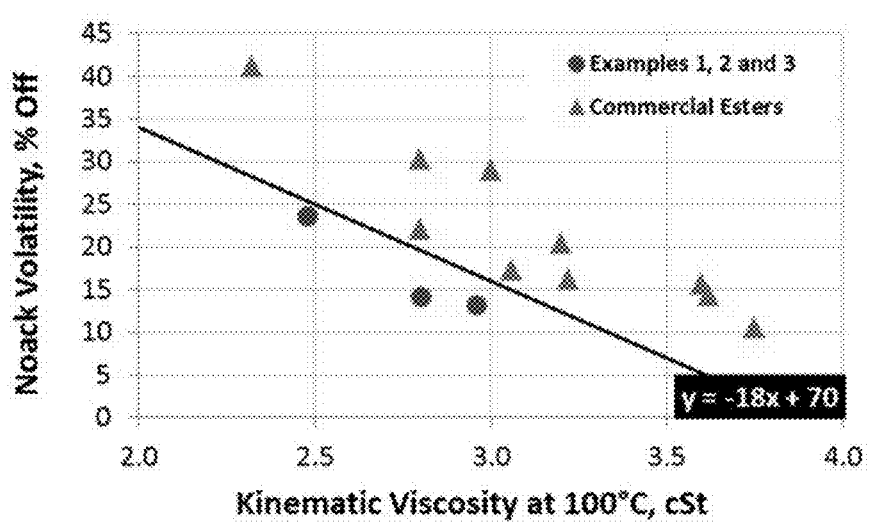
FIG. 2 graphically shows kinematic viscosity (100° C.) versus volatility (Noack) for selected base stocks of this disclosure and commercially available ester base stocks based on data in FIG. 1 and in accordance with Example 4.

All numerical values within the detailed description and the claims herein are modified by "about" or "approximately" the indicated value, and take into account experimental error and variations that would be expected by a person having ordinary skill in the art.

The compositions of this disclosure are diesters. These compositions exhibit (1) outstanding low viscosity low volatility properties, (2) good high-temperature thermal and oxidative stability, (3) good solvency for polar additives, (4) good deposit control, and (5) traction benefits, which make them attractive as Group V synthetic base stocks in high performance, fuel economy lubricant applications.

Low viscosity base stocks (e.g., kinematic viscosity at 100° C., 2-3 cSt) currently available in the marketplace are too volatile (Noack >15-20%) to be used for formulating next-generation ultra-low viscosity engine oils (i.e., xxW-4→xxW-16). These base stocks (e.g., SpectraSyn™ 2, QHVI™ 3, bis-(2-ethylhexyl) adipate, di-2-ethylhexyl azelate, Esterex™ A32) are unable to provide formulated engine oils that also meet current volatility API specification. In addition, current Group V ester base stocks generally have poor high temperature oxidation stability which can cause operational problems in engine, potentially causing high deposit formation. The present disclosure identifies diesters that have desirable low viscosity and low volatility properties while exhibiting traction benefits, good deposit control behavior and good high-temperature thermal-oxidative stability, hence provides a solution to achieve enhanced fuel economy and energy efficiency. In addition, good solvency for commonly used polar additives and potentially good hydrolytic stability are other advantages of these compounds in base stock applications.

As indicated above, the compositions of this disclosure include, for example, one or more diester compounds represented by the formula

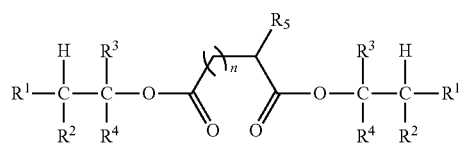

wherein each $R_1$ is independently a substituted or unsubstituted linear alkyl group ($C_1$-$C_{30}$), each $R_2$, $R_3$ and $R_4$ is hydrogen, $R_5$ is a substituted or unsubstituted alkyl group ($C_8$-$C_{30}$) or alkenyl group ($C_8$-$C_{30}$), and n is a value from about 0 to about 7. The composition has a viscosity ($Kv_{100}$) from about 1 cSt to about 10 cSt at 100° C. as determined by ASTM D445, a viscosity index (VI) from about −100 to about 300 as determined by ASTM D2270, and a Noack volatility of no greater than 50 percent as determined by ASTM D5800.

Preferred compositions of this disclosure include, for example, those wherein each $R_1$ is independently a substituted or unsubstituted linear alkyl group ($C_1$-$C_{20}$), each $R_2$, $R_3$ and $R_4$ is hydrogen, $R_5$ is a substituted or unsubstituted alkyl group ($C_8$-$C_{20}$) or alkenyl group ($C_8$-$C_{20}$), and n is a value from about 0 to about 7.

Other preferred compositions of this disclosure include, for example, those wherein each $R_1$ is independently a substituted or unsubstituted linear alkyl group ($C_1$-$C_{10}$), each $R_2$, $R_3$ and $R_4$ is hydrogen, $R_5$ is a substituted or unsubstituted alkyl group ($C_8$-$C_{10}$) or alkenyl group ($C_8$-$C_{10}$), and n is a value from about 0 to about 7.

Illustrative diester compositions of this disclosure have a viscosity ($Kv_{100}$) from about 1 cSt to about 8 cSt, more preferably from about 2 cSt to about 6 cSt, at 100° C. as determined by ASTM D445, a viscosity index (VI) from about −100 to about 300, more preferably from about 0 to about 200, even more preferably from about 25 to about 150, as determined by ASTM D2270, a Noack volatility of no greater than 25 percent, more preferably no greater than 20 percent, even more preferably no greater than 15 percent, as determined by ASTM D5800, and a high temperature high shear (HTHS) viscosity of less than about 2.5 cP, more preferably less than about 2.25 cP, even more preferably less than about 2.0 cP, as determined by ASTM D4683.

Preferred diester compositions of this disclosure have a high temperature high shear (HTHS) viscosity of less than about 1.7 cP as determined by ASTM D4683, and a Noack volatility from about 10 to about 30 percent as determined by ASTM D5800.

Illustrative diester compositions of this disclosure include, for example, dihexyl 2-octylsuccinate, diheptyl 2-octylsuccinate, and dipentyl 2-dodecylsuccinate, and the like.

The diester compositions of the present disclosure can be prepared by a process that involves reacting a substituted or unsubstituted alcohol with a substituted or unsubstituted carboxylic diacid or anhydride, optionally in the presence of a catalyst, under reaction conditions sufficient to produce one or more diester compositions.

Illustrative alcohols useful in the process of this disclosure include, for example, ethanol, propanol, isopropanol, butanol, isobutanol, isopentanol, 1-hexanol, 1-heptanol, 1-pentanol, 1-octanol, 2-ethylhexanol, 1-nonanol, isononanol, and the like.

Illustrative carboxylic diacids and anhydrides useful in the process of this disclosure include, for example, succinic anhydride, 2-methylsuccinic anhydride, 2-ethylsuccinic anhydride, 2-propylsuccinic anhydride, 2-hexylsuccinic anhydride, 2-octylsuccinic anhydride, 2-nonylsuccinic anhydride, 2-dodecylsuccinic anhydride, and the like, and succinic acid, 2-methylsuccinic acid, 2-ethylsuccinic acid, 2-propylsuccinic acid, 2-hexylsuccinic acid, 2-octylsuccinic acid, 2-nonylsuccinic acid, 2-dodecylsuccinic acid, adipic acid, 2-methyladipic acid, 2-ethyladipic acid, 2-propyladipic acid, 2-hexyladipic acid, 2-octyladipic acid, 2-nonyladipic acid, 2-dodecyladipic acid, malonic anhydride, alkylmalonic anhydride, malonic acid, alkylmalonic acid, azelaic acid, alkylazelaic acid, and the like.

Reaction conditions for the reaction of the alcohol with the carboxylic diacid or anhydride, such as temperature, pressure and contact time, may also vary greatly and any suitable combination of such conditions may be employed herein. The reaction temperature may range between about 25° C. to about 300° C., and preferably between about 50° C. to about 250° C., and more preferably between about 100° C. to about 200° C. Normally the reaction is carried out under ambient pressure and the contact time may vary from a matter of seconds or minutes to a few hours or greater. The reactants can be added to the reaction mixture or combined in any order. The reaction residence time employed can range from about 30 seconds to about 48 hours, preferably from about 5 minutes to 36 hours, and more preferably from about 1 hour to 24 hours.

As shown in the Examples herein, the diester compositions have more desirable viscosity-volatility characteristics when compared to commercially available low viscosity Group IV PAO synthetic base stocks (e.g., SpectraSyn™ 2, SpectraSyn™ 4)) or Group V ester base stocks (e.g., 2-ethylhexyl oleate, 2-ethylhexyl adipate, isodecyl adipate, 2-ethylhexyl phthalate, nC8/nC10 neopentyl glycol esters, nC7 trimethyolpropane ester, and the like). As shown in the Examples herein, the diester compositions of the present disclosure have lower viscosities than commercially available esters at similar volatility. Additionally, the diester compositions have lower volatility than commercially available esters at comparable viscosities.

As shown in the Examples herein, it has been discovered that formulated engine oils employing these diester compositions as a major component possess unexpectedly high thermal and oxidative stability along with good traction properties.

Furthermore, it has been found that these diester compositions also show high solvency for the typical additive components (e.g., antiwear additives, friction modifiers, dispersants, detergents, antioxidants, viscosity modifiers, pour point depressants, antifoaming agent, etc.) employed in the formulation of lubricants for PVL, CVL, as well as industrial applications.

Examples of techniques that can be employed to characterize the compositions formed by the process described above include, but are not limited to, analytical gas chromatography, nuclear magnetic resonance, thermogravimetric analysis (TGA), inductively coupled plasma mass spectrometry, differential scanning calorimetry (DSC), volatility and viscosity measurements.

This disclosure provides lubricating oils useful as engine oils and in other applications characterized by excellent oxidative stability. The lubricating oils are based on high quality base stocks including a major portion of a hydrocarbon base fluid such as a PAO or GTL with a secondary cobase stock component which is a diester as described herein. The lubricating oil base stock can be any oil boiling in the lube oil boiling range, typically between about 100 to 450° C. In the present specification and claims, the terms base oil(s) and base stock(s) are used interchangeably.

The viscosity-temperature relationship of a lubricating oil is one of the critical criteria which must be considered when selecting a lubricant for a particular application. Viscosity Index (VI) is an empirical, unitless number which indicates the rate of change in the viscosity of an oil within a given temperature range. Fluids exhibiting a relatively large change in viscosity with temperature are said to have a low viscosity index. A low VI oil, for example, will thin out at elevated temperatures faster than a high VI oil. Usually, the high VI oil is more desirable because it has higher viscosity at higher temperature, which translates into better or thicker lubrication film and better protection of the contacting machine elements.

In another aspect, as the oil operating temperature decreases, the viscosity of a high VI oil will not increase as much as the viscosity of a low VI oil. This is advantageous because the excessive high viscosity of the low VI oil will decrease the efficiency of the operating machine. Thus high VI (HVI) oil has performance advantages in both high and low temperature operation. VI is determined according to ASTM D2270. VI is related to kinematic viscosities measured at 40° C. and 100° C. using ASTM D445

Lubricating Oil Base Stocks

A wide range of lubricating oils is known in the art. Lubricating oils that are useful in the present disclosure are both natural oils and synthetic oils. Natural and synthetic oils (or mixtures thereof) can be used unrefined, refined, or rerefined (the latter is also known as reclaimed or reprocessed oil). Unrefined oils are those obtained directly from a natural or synthetic source and used without added purification. These include shale oil obtained directly from retorting operations, petroleum oil obtained directly from primary distillation, and ester oil obtained directly from an esterification process. Refined oils are similar to the oils discussed for unrefined oils except refined oils are subjected to one or more purification steps to improve the at least one lubricating oil property. One skilled in the art is familiar with many purification processes. These processes include solvent extraction, secondary distillation, acid extraction, base extraction, filtration, and percolation. Rerefined oils are obtained by processes analogous to refined oils but using an oil that has been previously used as a feed stock.

Groups I, II, III, IV and V are broad categories of base oil stocks developed and defined by the American Petroleum Institute (API Publication 1509; www.API.org) to create guidelines for lubricant base oils. Group I base stocks generally have a viscosity index of between about 80 to 120 and contain greater than about 0.03% sulfur and less than about 90% saturates. Group II base stocks generally have a viscosity index of between about 80 to 120, and contain less than or equal to about 0.03% sulfur and greater than or equal to about 90% saturates. Group III stock generally has a viscosity index greater than about 120 and contains less than or equal to about 0.03% sulfur and greater than about 90% saturates. Group IV includes polyalphaolefins (PAO). Group V base stocks include base stocks not included in Groups I-IV. The table below summarizes properties of each of these five groups.

| | Base Oil Properties | | |
|---|---|---|---|
| | Saturates | Sulfur | Viscosity Index |
| Group I | <90 and/or | >0.03% and | ≥80 and <120 |
| Group II | ≥90 and | ≤0.03% and | ≥80 and <120 |
| Group III | ≥90 and | ≤0.03% and | ≥120 |
| Group IV | Includes polyalphaolefins (PAO) products | | |
| Group V | All other base oil stocks not included in Groups I, II, III or IV | | |

Natural oils include animal oils, vegetable oils (castor oil and lard oil, for example), and mineral oils. Animal and vegetable oils possessing favorable thermal oxidative stability can be used. Of the natural oils, mineral oils are preferred. Mineral oils vary widely as to their crude source, for example, as to whether they are paraffinic, naphthenic, or mixed paraffinic-naphthenic. Oils derived from coal or shale are also useful in the present disclosure. Natural oils vary also as to the method used for their production and purification, for example, their distillation range and whether they are straight run or cracked, hydrorefined, or solvent extracted.

Group II and/or Group III hydroprocessed or hydrocracked base stocks, as well as synthetic oils such as polyalphaolefins, alkyl aromatics and synthetic esters, i.e. Group IV and Group V oils are also well known base stock oils.

Synthetic oils include hydrocarbon oil such as polymerized and interpolymerized olefins (polybutylenes, polypropylenes, propylene isobutylene copolymers, ethylene-olefin copolymers, and ethylene-alphaolefin copolymers, for example). Polyalphaolefin (PAO) oil base stocks, the Group IV API base stocks, are a commonly used synthetic hydrocarbon oil. By way of example, PAOs derived from $C_8$, $C_{10}$, $C_{12}$, $C_{14}$ olefins or mixtures thereof may be utilized. See U.S. Pat. Nos. 4,956,122; 4,827,064; and 4,827,073, which are incorporated herein by reference in their entirety. Group IV oils, that is, the PAO base stocks have viscosity indices preferably greater than 130, more preferably greater than 135, still more preferably greater than 140.

Esters may be useful in the lubricating oils of this disclosure. Additive solvency and seal compatibility characteristics may be secured by the use of esters such as the esters of dibasic acids with monoalkanols and the polyol esters of monocarboxylic acids. Esters of the former type include, for example, the esters of dicarboxylic acids such as phthalic acid, succinic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc.

Particularly useful synthetic esters are those which are obtained by reacting one or more polyhydric alcohols, preferably the hindered polyols such as the neopentyl polyols; e.g., neopentyl glycol, trimethylol ethane, 2-methyl-2-propyl-1,3-propanediol, trimethylol propane, pentaerythritol and dipentaerythritol with alkanoic acids containing at least about 4 carbon atoms, preferably $C_5$ to $C_{30}$ acids such as saturated straight chain fatty acids including caprylic acid, capric acids, lauric acid, myristic acid, palmitic acid, stearic acid, arachic acid, and behenic acid, or the corresponding branched chain fatty acids or unsaturated fatty acids such as oleic acid, or mixtures of any of these materials.

Esters should be used in an amount such that the improved wear and corrosion resistance provided by the lubricating oils of this disclosure are not adversely affected.

Non-conventional or unconventional base stocks and/or base oils include one or a mixture of base stock(s) and/or base oil(s) derived from: (1) one or more Gas-to-Liquids (GTL) materials, as well as (2) hydrodewaxed, or hydroisomerized/cat (and/or solvent) dewaxed base stock(s) and/or base oils derived from synthetic wax, natural wax or waxy feeds, mineral and/or non-mineral oil waxy feed stocks such as gas oils, slack waxes (derived from the solvent dewaxing of natural oils, mineral oils or synthetic oils; e.g., Fischer-Tropsch feed stocks), natural waxes, and waxy stocks such as gas oils, waxy fuels hydrocracker bottoms, waxy raffinate, hydrocrackate, thermal crackates, foots oil or other mineral, mineral oil, or even non-petroleum oil derived waxy materials such as waxy materials recovered from coal liquefaction or shale oil, linear or branched hydrocarbyl compounds with carbon number of about 20 or greater, preferably about 30 or greater and mixtures of such base stocks and/or base oils.

GTL materials are materials that are derived via one or more synthesis, combination, transformation, rearrangement, and/or degradation/deconstructive processes from gaseous carbon-containing compounds, hydrogen-containing compounds and/or elements as feed stocks such as hydrogen, carbon dioxide, carbon monoxide, water, methane, ethane, ethylene, acetylene, propane, propylene, propyne, butane, butylenes, and butynes. GTL base stocks and/or base oils are GTL materials of lubricating viscosity that are generally derived from hydrocarbons; for example, waxy synthesized hydrocarbons, that are themselves derived from simpler gaseous carbon-containing compounds, hydrogen-containing compounds and/or elements as feed stocks. GTL base stock(s) and/or base oil(s) include oils boiling in the lube oil boiling range (1) separated/fractionated from synthesized GTL materials such as, for example, by distillation and subsequently subjected to a final wax processing step which involves either or both of a catalytic dewaxing process, or a solvent dewaxing process, to produce lube oils of reduced/low pour point; (2) synthesized wax isomerates, comprising, for example, hydrodewaxed or hydroisomerized cat and/or solvent dewaxed synthesized wax or waxy hydrocarbons; (3) hydrodewaxed or hydroisomerized cat and/or solvent dewaxed Fischer-Tropsch (F-T) material (i.e., hydrocarbons, waxy hydrocarbons, waxes and possible analogous oxygenates); preferably hydrodewaxed or hydroisomerized/followed by cat and/or solvent dewaxing dewaxed F-T waxy hydrocarbons, or hydrodewaxed or hydroisomerized/followed by cat (or solvent) dewaxing dewaxed, F-T waxes, or mixtures thereof.

GTL base stock(s) and/or base oil(s) derived from GTL materials, especially, hydrodewaxed or hydroisomerized/followed by cat and/or solvent dewaxed wax or waxy feed, preferably F-T material derived base stock(s) and/or base oil(s), are characterized typically as having kinematic viscosities at 100° C. of from about 2 mm²/s to about 50 mm²/s (ASTM D445). They are further characterized typically as having pour points of −5° C. to about −40° C. or lower (ASTM D97). They are also characterized typically as having viscosity indices of about 80 to about 140 or greater (ASTM D2270).

In addition, the GTL base stock(s) and/or base oil(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL base stock(s) and/or base oil(s) typically have very low sulfur and nitrogen content, generally containing less than about 10 ppm, and more typically less than about 5 ppm of each of these elements. The sulfur and nitrogen content of GTL base stock(s) and/or base oil(s) obtained from F-T material, especially F-T wax, is essentially nil. In addition, the absence of phosphorous and aromatics make this materially especially suitable for the formulation of low SAP products.

The term GTL base stock and/or base oil and/or wax isomerate base stock and/or base oil is to be understood as embracing individual fractions of such materials of wide viscosity range as recovered in the production process, mixtures of two or more of such fractions, as well as mixtures of one or two or more low viscosity fractions with one, two or more higher viscosity fractions to produce a blend wherein the blend exhibits a target kinematic viscosity.

The GTL material, from which the GTL base stock(s) and/or base oil(s) is/are derived is preferably an F-T material (i.e., hydrocarbons, waxy hydrocarbons, wax).

Base oils for use in the formulated lubricating oils useful in the present disclosure are any of the variety of oils corresponding to API Group I, Group II, Group III, Group IV, Group V and Group VI oils and mixtures thereof, preferably API Group II, Group III, Group IV, Group V and Group VI oils and mixtures thereof, more preferably the Group III to Group VI base oils due to their exceptional volatility, stability, viscometric and cleanliness features. Minor quantities of Group I stock, such as the amount used to dilute additives for blending into formulated lube oil products, can be tolerated but should be kept to a minimum, i.e. amounts only associated with their use as diluent/carrier oil for additives used on an "as received" basis. Even in regard to the Group II stocks, it is preferred that the Group II stock be in the higher quality range associated with that stock, i.e. a Group II stock having a viscosity index in the range 100<VI<120.

In addition, the GTL base stock(s) and/or base oil(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL base stock(s) and/or base oil(s) and hydrodewaxed, or hydroisomerized/cat (and/or solvent) dewaxed base stock(s) and/or base oil(s) typically have very low sulfur and nitrogen content, generally containing less than about 10 ppm, and more typically less than about 5 ppm of each of these elements. The sulfur and nitrogen content of GTL base stock(s) and/or base oil(s) obtained from F-T material, especially F-T wax, is essentially nil. In addition, the absence of phosphorous and aromatics make this material especially suitable for the formulation of low sulfur, sulfated ash, and phosphorus (low SAP) products.

The base stock component of the present lubricating oils will typically be from 1 to 99 weight percent of the total composition (all proportions and percentages set out in this specification are by weight unless the contrary is stated) and more preferably usually in the range of 10 to 99 weight percent, or more preferably from 15 to 80 percent, or more preferably from 20 to 70 percent, or more preferably from 25 to 60 percent, or more preferably from 30 to 50 percent.

Diester Base Stock and Cobase Stock Components

Diester base stock and cobase stock components useful in this disclosure include, for example, compositions containing one or more compounds represented by the formula

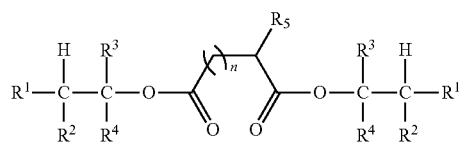

wherein each $R_1$ is independently a substituted or unsubstituted linear alkyl group ($C_1$-$C_{30}$), each $R_2$, $R_3$ and $R_4$ is hydrogen, $R_5$ is a substituted or unsubstituted alkyl group ($C_8$-$C_{30}$) or alkenyl group ($C_8$-$C_{30}$), and n is a value from about 0 to about 7. The composition has a viscosity ($Kv_{100}$) from about 1 cSt to about 10 cSt at 100° C. as determined by ASTM D445, a viscosity index (VI) from about −100 to about 300 as determined by ASTM D2270, and a Noack volatility of no greater than 50 percent as determined by ASTM D5800.

Preferred diester base stock and cobase stock components of this disclosure include, for example, those wherein each $R_1$ is independently a substituted or unsubstituted linear alkyl group ($C_1$-$C_{20}$), each $R_2$, $R_3$ and $R_4$ is hydrogen, $R_5$ is a substituted or unsubstituted alkyl group ($C_8$-$C_{20}$) or alkenyl group ($C_8$-$C_{20}$), and n is a value from about 0 to about 7.

Other preferred diester base stock and cobase stock components of this disclosure include, for example, those wherein each $R_1$ is independently a substituted or unsubstituted linear alkyl group ($C_1$-$C_{10}$), each $R_2$, $R_3$ and $R_4$ is hydrogen, $R_5$ is a substituted or unsubstituted alkyl group ($C_8$-$C_{10}$) or alkenyl group ($C_8$-$C_{10}$), and n is a value from about 0 to about 7.

Illustrative diester base stock and cobase stock components of this disclosure have a viscosity ($Kv_{100}$) from about 1 cSt to about 8 cSt, more preferably from about 2 cSt to about 6 cSt, at 100° C. as determined by ASTM D445, a viscosity index (VI) from about −100 to about 300, more preferably from about 0 to about 200, even more preferably from about 25 to about 150, as determined by ASTM D2270, a Noack volatility of no greater than 25 percent, more preferably no greater than 20 percent, even more preferably no greater than 15 percent, as determined by ASTM D5800, and a high temperature high shear (HTHS) viscosity of less than about 2.5 cP, more preferably less than about 2.25 cP, even more preferably less than about 2.0 cP, as determined by ASTM D4683.

Preferred diester base stock and cobase stock components of this disclosure have a high temperature high shear (HTHS) viscosity of less than about 1.7 cP as determined by ASTM D4683, and a Noack volatility from about 10 to about 30 percent as determined by ASTM D5800.

Illustrative diester base stock and cobase stock components of this disclosure include, for example, dihexyl 2-octylsuccinate, diheptyl 2-octylsuccinate, and dipentyl 2-dodecylsuccinate, and the like.

The diester base stock and cobase stock components of the present disclosure can be prepared by a process that involves reacting a substituted or unsubstituted alcohol with a substituted or unsubstituted carboxylic diacid or anhydride, optionally in the presence of a catalyst, under reaction conditions sufficient to produce one or more diester base stock and cobase stock components.

Illustrative alcohols useful in the process of this disclosure include, for example, ethanol, propanol, isopropanol, butanol, isobutanol, isopentanol, 1-hexanol, 1-heptanol, 1-pentanol, 1-octanol, 2-ethylhexanol, 1-nonanol, isononanol, and the like.

Illustrative carboxylic diacids and anhydrides useful in the process of this disclosure include, for example, succinic anhydride, 2-methylsuccinic anhydride, 2-ethylsuccinic anhydride, 2-propylsuccinic anhydride, 2-hexylsuccinic anhydride, 2-octylsuccinic anhydride, 2-nonylsuccinic anhydride, 2-dodecylsuccinic anhydride, and the like, and succinic acid, 2-methylsuccinic acid, 2-ethylsuccinic acid, 2-propylsuccinic acid, 2-hexylsuccinic acid, 2-octylsuccinic acid, 2-nonylsuccinic acid, 2-dodecylsuccinic acid, adipic acid, 2-methyladipic acid, 2-ethyladipic acid, 2-propyladipic acid, 2-hexyladipic acid, 2-octyladipic acid, 2-nonyladipic acid, 2-dodecyladipic acid, malonic anhydride, alkylmalonic anhydride, malonic acid, alkylmalonic acid, azelaic acid, alkylazelaic acid, and the like.

Reaction conditions for the reaction of the alcohol with the carboxylic diacid or anhydride, such as temperature, pressure and contact time, may also vary greatly and any suitable combination of such conditions may be employed herein. The reaction temperature may range between about 25° C. to about 300° C., and preferably between about 50° C. to about 250° C., and more preferably between about 100° C. to about 200° C. Normally the reaction is carried out under ambient pressure and the contact time may vary from a matter of seconds or minutes to a few hours or greater. The reactants can be added to the reaction mixture or combined in any order. The reaction residence time employed can range from about 30 seconds to about 48 hours, preferably from about 5 minutes to 36 hours, and more preferably from about 1 hour to 24 hours.

The diester cobase stock component is preferably present in an amount sufficient for providing oxidative stability in the lubricating oil. The diester cobase stock can be present as the major base stock in the lubricating oils of this disclosure. Accordingly, the diester can be present in an amount from about 1 to about 99 weight percent, preferably from about 5 to about 99 weight percent, and more preferably from about 10 to about 99 weight percent, or more preferably from 40 to 90 percent, or more preferably from 50 to 80 percent, or more preferably from 60 to 80 percent.

The diester cobase stock component can also be present as a minor co-base stock in the lubricating oils of this disclosure. Accordingly, the diester cobase stock of the present lubricating oils will typically be present from 1 to 50 weight percent, or more preferably from 5 to 50 percent, or more preferably from 10 to 40 percent, or more preferably from 20 to 30 percent.

Other Additives

The formulated lubricating oil useful in the present disclosure may additionally contain one or more of the other commonly used lubricating oil performance additives including but not limited to dispersants, other detergents, corrosion inhibitors, rust inhibitors, metal deactivators, other anti-wear agents and/or extreme pressure additives, anti-seizure agents, wax modifiers, viscosity index improvers, viscosity modifiers, fluid-loss additives, seal compatibility agents, other friction modifiers, lubricity agents, anti-staining agents, chromophoric agents, defoamants, demulsifiers, emulsifiers, densifiers, wetting agents, gelling agents, tackiness agents, colorants, and others. For a review of many commonly used additives, see Klamann in Lubricants and Related Products, Verlag Chemie, Deerfield Beach, Fla.; ISBN 0-89573-177-0. Reference is also made to "Lubricant Additives Chemistry and Applications" edited by Leslie R. Rudnick, Marcel Dekker, Inc. New York, 2003 ISBN: 0-8247-0857-1.

All of the additives described below can be used alone or in combination. The total treat rates for the additives can range from 1 to 30 percent, or more preferably from 2 to 25 percent, or more preferably from 3 to 20 percent, or more preferably from 4 to 15 percent, or more preferably from 5 to 10 percent. Particularly preferred compositions have additive levels between 15 and 20 percent.

The types and quantities of performance additives used in combination with the instant disclosure in lubricant compositions are not limited by the examples shown herein as illustrations.

Viscosity Modifiers

Viscosity modifiers (also known as viscosity index improvers—VI improvers—and viscosity improvers) can be included in the lubricant compositions of this disclosure.

Viscosity modifiers provide lubricants with high and low temperature operability. These additives impart shear stability at elevated temperatures and acceptable viscosity at low temperatures.

Suitable viscosity modifiers include high molecular weight hydrocarbons, polyesters and viscosity modifier dispersants that function as both a viscosity modifier and a dispersant. Typical molecular weights of these polymers are between about 10,000 to 1,500,000, more typically about 20,000 to 1,200,000, and even more typically between about 50,000 and 1,000,000.

Examples of suitable viscosity modifiers are linear or star-shaped polymers and copolymers of methacrylate, butadiene, olefins, or alkylated styrenes. Polyisobutylene is a commonly used viscosity modifier. Another suitable viscosity modifier is polymethacrylate (copolymers of various chain length alkyl methacrylates, for example), some formulations of which also serve as pour point depressants. Other suitable viscosity modifiers include copolymers of ethylene and propylene, hydrogenated block copolymers of styrene and isoprene, and polyacrylates (copolymers of various chain length acrylates, for example). Specific examples include styrene-isoprene or styrene-butadiene based polymers of 50,000 to 200,000 molecular weight.

Olefin copolymers are commercially available from Chevron Oronite Company LLC under the trade designation "PARATONE®" (such as "PARATONE® 8921" and "PARATONE® 8941"); from Afton Chemical Corporation under the trade designation "HiTEC®" (such as "HiTEC® 5850B"; and from The Lubrizol Corporation under the trade designation "Lubrizol® 7067C". Hydrogenated polyisoprene star polymers are commercially available from Infineum International Limited, e.g., under the trade designation "SV200" and "SV600". Hydrogenated diene-styrene block copolymers are commercially available from Infineum International Limited, e.g., under the trade designation "SV 50".

The polymethacrylate or polyacrylate polymers can be linear polymers which are available from Evnoik Industries under the trade designation "Viscoplex®" (e.g., Viscoplex 6-954) or star polymers which are available from Lubrizol Corporation under the trade designation Asteric™ (e.g., Lubrizol 87708 and Lubrizol 87725).

Illustrative vinyl aromatic-containing polymers useful in this disclosure may be derived predominantly from vinyl aromatic hydrocarbon monomer. Illustrative vinyl aromatic-containing copolymers useful in this disclosure may be represented by the following general formula:

A-B wherein A is a polymeric block derived predominantly from vinyl aromatic hydrocarbon monomer, and B is a polymeric block derived predominantly from conjugated diene monomer.

The vinyl aromatic-containing polymers or copolymers useful in this disclosure have a weight average molecular weight greater than about 80,000, and a number average molecular weight greater than about 40,000; preferably a weight average molecular weight greater than about 90,000, and a number average molecular weight greater than about 75,000; and more preferably a weight average molecular weight greater than about 100,000 and less than 1,000,000, and a number average molecular weight greater than about 100,000 and less than 1,000,000. The vinyl aromatic-containing polymers or copolymers have an amount of vinyl aromatic content greater than about 10% by weight, or greater than about 20% by weight, or greater than about 30% by weight, of the vinyl aromatic-containing polymer or copolymer. The vinyl aromatic-containing polymers or copolymers have an amount of vinyl aromatic content preferably between about 10% and about 50% by weight, more preferably between about 15% and about 40% by weight, and even more preferably between about 20% and about 35% by weight, of the vinyl aromatic-containing polymer or copolymer.

In an embodiment of this disclosure, the viscosity modifiers may be used in an amount of less than about 2.0 weight percent, preferably less than about 1.0 weight percent, and more preferably less than about 0.5 weight percent, based on the total weight of the formulated oil or lubricating engine oil. Viscosity modifiers are typically added as concentrates, in large amounts of diluent oil.

In another embodiment of this disclosure, the viscosity modifiers may be used in an amount of from 0.05 to about 2.0 weight percent, preferably 0.15 to about 1.0 weight percent, and more preferably 0.25 to about 0.5 weight percent, based on the total weight of the formulated oil or lubricating engine oil. Or the viscosity modifiers may be used in an amount (total solid polymer content) of from 0.5 to about 2.0 weight percent, preferably 0.8 to about 1.5 weight percent, and more preferably 1.0 to about 1.3 weight percent, based on the total weight of the formulated oil or lubricating engine oil.

As used herein, the viscosity modifier concentrations are given on an "as delivered" basis. Typically, the active polymer is delivered with a diluent oil. The "as delivered" viscosity modifier typically contains from 20 weight percent to 75 weight percent of an active polymer for polymethacrylate or polyacrylate polymers, or from 8 weight percent to 20 weight percent of an active polymer for olefin copolymers, hydrogenated polyisoprene star polymers, or hydrogenated diene-styrene block copolymers, in the "as delivered" polymer concentrate.

Antioxidants

Typical anti-oxidant include phenolic anti-oxidants, aminic anti-oxidants and oil-soluble copper complexes.

The phenolic antioxidants include sulfurized and non-sulfurized phenolic antioxidants. The terms "phenolic type" or "phenolic antioxidant" used herein includes compounds having one or more than one hydroxyl group bound to an aromatic ring which may itself be mononuclear, e.g., benzyl, or poly-nuclear, e.g., naphthyl and spiro aromatic compounds. Thus "phenol type" includes phenol per se, catechol, resorcinol, hydroquinone, naphthol, etc., as well as alkyl or alkenyl and sulfurized alkyl or alkenyl derivatives thereof, and bisphenol type compounds including such biphenol compounds linked by alkylene bridges sulfuric bridges or oxygen bridges. Alkyl phenols include mono- and poly-alkyl or alkenyl phenols, the alkyl or alkenyl group containing from about 3-100 carbons, preferably 4 to 50 carbons and sulfurized derivatives thereof, the number of alkyl or alkenyl groups present in the aromatic ring ranging from 1 to up to the available unsatisfied valences of the aromatic ring remaining after counting the number of hydroxyl groups bound to the aromatic ring.

Generally, therefore, the phenolic anti-oxidant may be represented by the general formula:

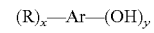

$(R)_x$—Ar—$(OH)_y$ where Ar is selected from the group consisting of:

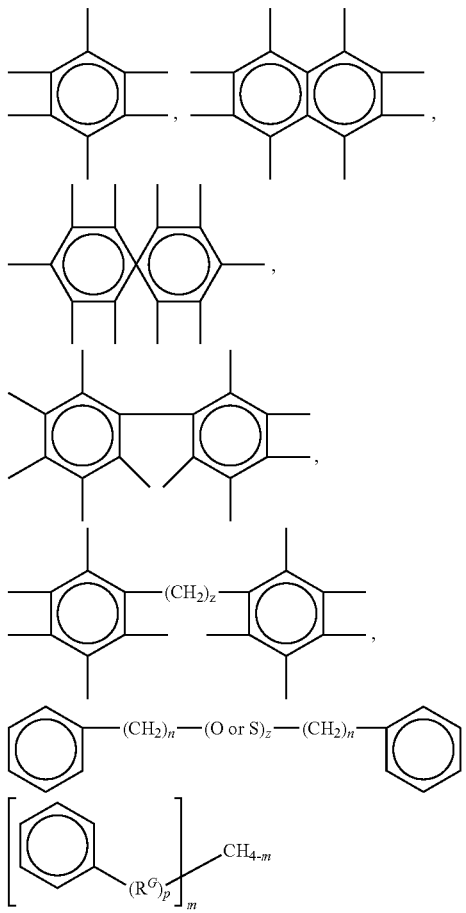

wherein R is a $C_3$-$C_{100}$ alkyl or alkenyl group, a sulfur substituted alkyl or alkenyl group, preferably a $C_4$-$C_{50}$ alkyl or alkenyl group or sulfur substituted alkyl or alkenyl group, more preferably $C_3$-$C_{100}$ alkyl or sulfur substituted alkyl group, most preferably a $C_4$-$C_{50}$ alkyl group, $R^G$ is a $C_1$-$C_{100}$ alkylene or sulfur substituted alkylene group, preferably a $C_2$-$C_{50}$ alkylene or sulfur substituted alkylene group, more preferably a $C_2$-$C_2$ alkylene or sulfur substituted alkylene group, y is at least 1 to up to the available valences of Ar, x ranges from 0 to up to the available valances of Ar-y, z ranges from 1 to 10, n ranges from 0 to 20, and m is 0 to 4 and p is 0 or 1, preferably y ranges from 1 to 3, x ranges from 0 to 3, z ranges from 1 to 4 and n ranges from 0 to 5, and p is 0.

Preferred phenolic anti-oxidant compounds are the hindered phenolics and phenolic esters which contain a sterically hindered hydroxyl group, and these include those derivatives of dihydroxy aryl compounds in which the hydroxyl groups are in the o- or p-position to each other. Typical phenolic anti-oxidants include the hindered phenols substituted with $C_1$+ alkyl groups and the alkylene coupled derivatives of these hindered phenols. Examples of phenolic materials of this type 2-t-butyl-4-heptyl phenol; 2-t-butyl-4-octyl phenol; 2-t-butyl-4-dodecyl phenol; 2,6-di-t-butyl-4-heptyl phenol; 2,6-di-t-butyl-4-dodecyl phenol; 2-methyl-6-t-butyl-4-heptyl phenol; 2-methyl-6-t-butyl-4-dodecyl phenol; 2,6-di-t-butyl-4 methyl phenol; 2,6-di-t-butyl-4-ethyl phenol; and 2,6-di-t-butyl 4 alkoxy phenol; and

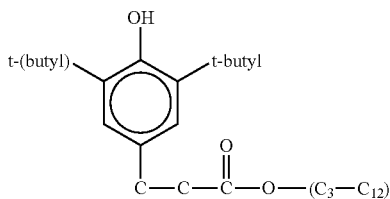

Phenolic type anti-oxidants are well known in the lubricating industry and commercial examples such as Ethanox® 4710, Irganox® 1076, Irganox® L1035, Irganox® 1010, Irganox® L109, Irganox® L118, Irganox® L135 and the like are familiar to those skilled in the art. The above is presented only by way of exemplification, not limitation on the type of phenolic anti-oxidants which can be used.

The phenolic anti-oxidant can be employed in an amount in the range of about 0.1 to 3 wt %, preferably about 1 to 3 wt %, more preferably 1.5 to 3 wt % on an active ingredient basis.

Aromatic amine anti-oxidants include phenyl-a-naphthyl amine which is described by the following molecular structure:

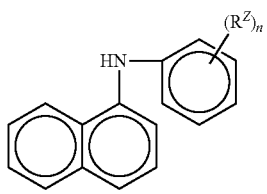

wherein $R^z$ is hydrogen or a $C_1$ to $C_{14}$ linear or $C_3$ to $C_{14}$ branched alkyl group, preferably $C_1$ to $C_{10}$ linear or $C_3$ to $C_{10}$ branched alkyl group, more preferably linear or branched $C_6$ to $C_8$ and n is an integer ranging from 1 to 5 preferably 1. A particular example is Irganox L06.

Other aromatic amine anti-oxidants include other alkylated and non-alkylated aromatic amines such as aromatic monoamines of the formula $R^8R^9R^{10}N$ where $R^8$ is an aliphatic, aromatic or substituted aromatic group, $R^9$ is an aromatic or a substituted aromatic group, and $R^{10}$ is H, alkyl, aryl or $R^{11}S(O)_xR^{12}$ where $R^{11}$ is an alkylene, alkenylene, or aralkylene group, $R^{12}$ is a higher alkyl group, or an alkenyl, aryl, or alkaryl group, and x is 0, 1 or 2. The aliphatic group $R^8$ may contain from 1 to about 20 carbon atoms, and preferably contains from about 6 to 12 carbon atoms. The aliphatic group is a saturated aliphatic group. Preferably, both $R^8$ and $R^9$ are aromatic or substituted aromatic groups, and the aromatic group may be a fused ring aromatic group such as naphthyl. Aromatic groups $R^8$ and $R^9$ may be joined together with other groups such as S.

Typical aromatic amines anti-oxidants have alkyl substituent groups of at least about 6 carbon atoms. Examples of aliphatic groups include hexyl, heptyl, octyl, nonyl, and decyl. Generally, the aliphatic groups will not contain more than about 14 carbon atoms. The general types of such other additional amine anti-oxidants which may be present include diphenylamines, phenothiazines, imidodibenzyls and diphenyl phenylene diamines. Mixtures of two or more of such other additional aromatic amines may also be present. Polymeric amine antioxidants can also be used.

Another class of anti-oxidant used in lubricating oil compositions and which may also be present are oil-soluble copper compounds. Any oil-soluble suitable copper compound may be blended into the lubricating oil. Examples of suitable copper antioxidants include copper dihydrocarbyl thio- or dithio-phosphates and copper salts of carboxylic acid (naturally occurring or synthetic). Other suitable copper salts include copper dithiocarbamates, sulphonates, phenates, and acetylacetonates. Basic, neutral, or acidic copper Cu(I) and or Cu(II) salts derived from alkenyl succinic acids or anhydrides are known to be particularly useful.

Such antioxidants may be used individually or as mixtures of one or more types of antioxidants, the total amount employed being an amount of about 0.50 to 5 wt %, preferably about 0.75 to 3 wt % (on an as-received basis).

Detergents

Illustrative detergents useful in this disclosure include, for example, alkali metal detergents, alkaline earth metal detergents, or mixtures of one or more alkali metal detergents and one or more alkaline earth metal detergents. Oils formulated with low concentrations of detergents and/or low ash detergents can be preferred as low ash, low metals, low phosphorus oils. A typical detergent is an anionic material that contains a long chain hydrophobic portion of the molecule and a smaller anionic or oleophobic hydrophilic portion of the molecule. The anionic portion of the detergent is typically derived from an organic acid such as a sulfur acid, carboxylic acid, phosphorous acid, phenol, or mixtures thereof. The counterion is typically an alkaline earth or alkali metal.

Salts that contain a substantially stoichiometric amount of the metal are described as neutral salts and have a total base number (TBN, as measured by ASTM D2896) of from 0 to 80. Many compositions are overbased, containing large amounts of a metal base that is achieved by reacting an excess of a metal compound (a metal hydroxide or oxide, for example) with an acidic gas (such as carbon dioxide). Useful detergents can be neutral, mildly overbased, or highly overbased. These detergents can be used in mixtures of neutral, overbased, highly overbased calcium salicylate, sulfonates, phenates and/or magnesium salicylate, sulfonates, phenates. The TBN ranges can vary from low, medium to high TBN products, including as low as 0 to as high as 600. Mixtures of low, medium, high TBN can be used, along with mixtures of calcium and magnesium metal based detergents, and including sulfonates, phenates, salicylates, and carboxylates. A detergent mixture with a metal ratio of 1, in conjunction of a detergent with a metal ratio of 2, and as high as a detergent with a metal ratio of 5, can be used. Borated detergents can also be used.

Alkaline earth phenates are another useful class of detergent. These detergents can be made by reacting alkaline earth metal hydroxide or oxide (CaO, Ca(OH)2, BaO, Ba(OH)2, MgO, Mg(OH)2, for example) with an alkyl phenol or sulfurized alkylphenol. Useful alkyl groups include straight chain or branched C1-C30 alkyl groups, preferably, C4-C20 or mixtures thereof. Examples of suitable phenols include isobutylphenol, 2-ethylhexylphenol, nonylphenol, dodecyl phenol, and the like. It should be noted that starting alkylphenols may contain more than one alkyl substituent that are each independently straight chain or branched and can be used from 0.5 to 6 weight percent. When a non-sulfurized alkylphenol is used, the sulfurized product may be obtained by methods well known in the art. These methods include heating a mixture of alkylphenol and sulfurizing agent (including elemental sulfur, sulfur halides such as sulfur dichloride, and the like) and then reacting the sulfurized phenol with an alkaline earth metal base.

Metal salts of carboxylic acids are also useful as detergents. These carboxylic acid detergents may be prepared by reacting a basic metal compound with at least one carboxylic acid and removing free water from the reaction product. These compounds may be overbased to produce the desired TBN level. Detergents made from salicylic acid are one preferred class of detergents derived from carboxylic acids. Useful salicylates include long chain alkyl salicylates. One useful family of compositions is of the formula

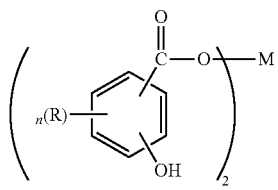

where R is an alkyl group having 1 to about 30 carbon atoms, n is an integer from 1 to 4, and M is an alkaline earth metal. Preferred R groups are alkyl chains of at least C11, preferably C13 or greater. R may be optionally substituted with substituents that do not interfere with the detergent's function. M is preferably, calcium, magnesium, or barium. More preferably, M is calcium or magnesium.

Hydrocarbyl-substituted salicylic acids may be prepared from phenols by the Kolbe reaction (see U.S. Pat. No. 3,595,791). The metal salts of the hydrocarbyl-substituted salicylic acids may be prepared by double decomposition of a metal salt in a polar solvent such as water or alcohol.

Alkaline earth metal phosphates are also used as detergents and are known in the art.

Detergents may be simple detergents or what is known as hybrid or complex detergents. The latter detergents can provide the properties of two detergents without the need to blend separate materials. See U.S. Pat. No. 6,034,039.

Preferred detergents include calcium phenates, calcium sulfonates, calcium salicylates, magnesium phenates, magnesium sulfonates, magnesium salicylates and other related components (including borated detergents), and mixtures thereof. Preferred mixtures of detergents include magnesium sulfonate and calcium salicylate, magnesium sulfonate and calcium sulfonate, magnesium sulfonate and calcium phenate, calcium phenate and calcium salicylate, calcium phenate and calcium sulfonate, calcium phenate and magnesium salicylate, calcium phenate and magnesium phenate.

The lubricating oils of this disclosure exhibit desired properties, e.g., wear control, deposit control and fuel efficiency, in the presence or absence of a detergent, in particular, the presence or absence of a salicylate detergent or a sulfonate detergent.

The detergent concentration in the lubricating oils of this disclosure can range from about 0.5 to about 20 weight percent or more, preferably about 0.6 to 5.0 weight percent, and more preferably from about 0.8 weight percent to about 4.0 weight percent, based on the total weight of the lubricating oil.

As used herein, the detergent concentrations are given on an "as delivered" basis. Typically, the active detergent is delivered with a process oil. The "as delivered" detergent typically contains from about 20 weight percent to about 100 weight percent, or from about 40 weight percent to about 60 weight percent, of active detergent in the "as delivered" detergent product.

Dispersants

During engine operation, oil-insoluble oxidation byproducts are produced. Dispersants help keep these byproducts in solution, thus diminishing their deposition on metal surfaces. Dispersants may be ashless or ash-forming in nature. Preferably, the dispersant is ashless. So called ashless dispersants are organic materials that form substantially no ash upon combustion. For example, non-metal-containing or borated metal-free dispersants are considered ashless. In contrast, metal-containing detergents discussed above form ash upon combustion.

Suitable dispersants typically contain a polar group attached to a relatively high molecular weight hydrocarbon chain. The polar group typically contains at least one element of nitrogen, oxygen, or phosphorus. Typical hydrocarbon chains contain 50 to 400 carbon atoms.

A particularly useful class of dispersants are the alkenyl-succinic derivatives, typically produced by the reaction of a long chain substituted alkenyl succinic compound, usually a substituted succinic anhydride, with a polyhydroxy or polyamino compound. The long chain group constituting the oleophilic portion of the molecule which confers solubility in the oil, is normally a polyisobutylene group. Many examples of this type of dispersant are well known commercially and in the literature. Exemplary patents describing such dispersants are U.S. Pat. Nos. 3,172,892; 3,219,666; 3,316,177 and 4,234,435. Other types of dispersants are described in U.S. Pat. Nos. 3,036,003; and 5,705,458.

Hydrocarbyl-substituted succinic acid compounds are popular dispersants. In particular, succinimide, succinate esters, or succinate ester amides prepared by the reaction of a hydrocarbon-substituted succinic acid compound preferably having at least 50 carbon atoms in the hydrocarbon substituent, with at least one equivalent of an alkylene amine are particularly useful.

Succinimides are formed by the condensation reaction between alkenyl succinic anhydrides and amines. Molar ratios can vary depending on the amine or polyamine. For example, the molar ratio of alkenyl succinic anhydride to TEPA can vary from about 1:1 to about 5:1 or more.

Succinate esters are formed by the condensation reaction between alkenyl succinic anhydrides and alcohols or polyols. Molar ratios can vary depending on the alcohol or polyol used. For example, the condensation product of an alkenyl succinic anhydride and pentaerythritol is a useful dispersant.

Succinate ester amides are formed by condensation reaction between alkenyl succinic anhydrides and alkanol amines. For example, suitable alkanol amines include ethoxylated polyalkylpolyamines, propoxylated polyalkylpolyamines and polyalkenylpolyamines such as polyethylene polyamines. One example is propoxylated hexamethylenediamine.

The molecular weight of the alkenyl succinic anhydrides will typically range between 400 and 5,000 with preferred ranges between 800 and 2,500. The above products can be post-reacted with various reagents such as sulfur, oxygen, formaldehyde, carboxylic acids such as oleic acid, and boron compounds such as borate esters or highly borated dispersants. The dispersants can be borated with from about 0.1 to about 5 moles of boron per mole of dispersant reaction product.

Mannich base dispersants are made from the reaction of alkylphenols, formaldehyde, and amines. Process aids and catalysts, such as oleic acid and sulfonic acids, can also be part of the reaction mixture. Molecular weights of the alkylphenols range from 800 to 2,500. Mannich base dispersants can also be borated and mixtures of Mannich base dispersants can be used.

Typical high molecular weight aliphatic acid modified Mannich condensation products can be prepared from high molecular weight alkyl-substituted hydroxyaromatics or $HN(R)_2$ group-containing reactants.

Examples of high molecular weight alkyl-substituted hydroxyaromatic compounds are polypropylphenol, polybutylphenol, and other polyalkylphenols. These polyalkylphenols can be obtained by the alkylation, in the presence of an alkylating catalyst, such as $BF_3$, of phenol with high molecular weight polypropylene, polybutylene, and other polyalkylene compounds to give alkyl substituents on the benzene ring of phenol having an average 600-100,000 molecular weight.

Examples of $HN(R)_2$ group-containing reactants are alkylene polyamines, principally polyethylene polyamines. Other representative organic compounds containing at least one $HN(R)_2$ group suitable for use in the preparation of Mannich condensation products are well known and include the mono- and di-amino alkanes and their substituted analogs, e.g., ethylamine and diethanol amine; aromatic diamines, e.g., phenylene diamine, diamino naphthalenes; heterocyclic amines, e.g., morpholine, pyrrole, pyrrolidine, imidazole, imidazolidine, and piperidine; melamine and their substituted analogs.

Examples of alkylene polyamine reactants include ethylenediamine, diethylene triamine, triethylene tetraamine, tetraethylene pentaamine, pentaethylene hexamine, hexaethylene heptaamine, heptaethylene octaamine, octaethylene nonaamine, nonaethylene decamine, and decaethylene undecamine and mixture of such amines having nitrogen contents corresponding to the alkylene polyamines, in the formula $H_2N-(Z-NH-)_nH$, mentioned before, Z is a divalent ethylene and n is 1 to 10 of the foregoing formula. Corresponding propylene polyamines such as propylene diamine and di-, tri-, tetra-, pentapropylene tri-, tetra-, penta- and hexaamines are also suitable reactants. The alkylene polyamines are usually obtained by the reaction of ammonia and dihalo alkanes, such as dichloro alkanes. Thus the alkylene polyamines obtained from the reaction of 2 to 11 moles of ammonia with 1 to 10 moles of dichloroalkanes having 2 to 6 carbon atoms and the chlorines on different carbons are suitable alkylene polyamine reactants.

Aldehyde reactants useful in the preparation of the high molecular products useful in this disclosure include the aliphatic aldehydes such as formaldehyde (also as paraformaldehyde and formalin), acetaldehyde and aldol (β-hydroxybutyraldehyde). Formaldehyde or a formaldehyde-yielding reactant is preferred.

Preferred dispersants include borated and non-borated succinimides, including those derivatives from mono-succinimides, bis-succinimides, and/or mixtures of mono- and bis-succinimides, wherein the hydrocarbyl succinimide is derived from a hydrocarbylene group such as polyisobutylene having a Mn of from about 500 to about 5000 or a mixture of such hydrocarbylene groups. Other preferred dispersants include succinic acid-esters and amides, alkylphenol-polyamine-coupled Mannich adducts, their capped derivatives, and other related components. Such additives may be used in an amount of about 0.1 to 20 wt %, preferably about 0.1 to 8 wt %, more preferably about 1 to 6 wt % (on an as-received basis) based on the weight of the total lubricant.

Pour Point Depressants

Conventional pour point depressants (also known as lube oil flow improvers) may also be present. Pour point depressant may be added to lower the minimum temperature at which the fluid will flow or can be poured. Examples of suitable pour point depressants include alkylated naphthalenes polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. Such additives may be used in amount of about 0.0 to 0.5 wt %, preferably about 0 to 0.3 wt %, more preferably about 0.001 to 0.1 wt % on an as-received basis.

Corrosion Inhibitors/Metal Deactivators

Corrosion inhibitors are used to reduce the degradation of metallic parts that are in contact with the lubricating oil composition. Suitable corrosion inhibitors include aryl thiazines, alkyl substituted dimercapto thiodiazoles thiadiazoles and mixtures thereof. Such additives may be used in an amount of about 0.01 to 5 wt %, preferably about 0.01 to 1.5 wt %, more preferably about 0.01 to 0.2 wt %, still more preferably about 0.01 to 0.1 wt % (on an as-received basis) based on the total weight of the lubricating oil composition.

Seal Compatibility Additives

Seal compatibility agents help to swell elastomeric seals by causing a chemical reaction in the fluid or physical change in the elastomer. Suitable seal compatibility agents for lubricating oils include organic phosphates, aromatic esters, aromatic hydrocarbons, esters (butylbenzyl phthalate, for example), and polybutenyl succinic anhydride and sulfolane-type seal swell agents such as Lubrizol 730-type seal swell additives. Such additives may be used in an amount of about 0.01 to 3 wt %, preferably about 0.01 to 2 wt % on an as-received basis.

Anti-Foam Agents

Anti-foam agents may advantageously be added to lubricant compositions. These agents retard the formation of stable foams. Silicones and organic polymers are typical anti-foam agents. For example, polysiloxanes, such as silicon oil or polydimethyl siloxane, provide antifoam properties. Anti-foam agents are commercially available and may be used in conventional minor amounts along with other additives such as demulsifiers; usually the amount of these additives combined is less than 1 percent, preferably 0.001 to about 0.5 wt %, more preferably about 0.001 to about 0.2 wt %, still more preferably about 0.0001 to 0.15 wt % (on an as-received basis) based on the total weight of the lubricating oil composition.

Inhibitors and Antirust Additives

Anti-rust additives (or corrosion inhibitors) are additives that protect lubricated metal surfaces against chemical attack by water or other contaminants. One type of anti-rust additive is a polar compound that wets the metal surface preferentially, protecting it with a film of oil. Another type of anti-rust additive absorbs water by incorporating it in a water-in-oil emulsion so that only the oil touches the surface. Yet another type of anti-rust additive chemically adheres to the metal to produce a non-reactive surface. Examples of suitable additives include zinc dithiophosphates, metal phenolates, basic metal sulfonates, fatty acids and amines. Such additives may be used in an amount of about 0.01 to 5 wt %, preferably about 0.01 to 1.5 wt % on an as-received basis.

ZDDP anti-wear additives are essential components of the present disclosure. ZDDP derived from C8 to C18 primary or secondary alcohols and preferably derived from C4, C5, and/or C7 primary or secondary alcohols and mixtures thereof are often preferred. In some applications, low phosphorus ZDDP additives with <0.10% by weight phosphorus, leading to about from 0.02% to 0.08% phosphorus in finished oils can be preferred. In addition to ZDDP, other anti-wear additives can be present, including zinc dithiocarbamates, molybdenum dialkyldithiophosphates, molybdenum dithiocarbamates, other organo molybdenum-nitrogen complexes, sulfurized olefins, etc.

The term "organo molybdenum-nitrogen complexes" embraces the organo molybdenum-nitrogen complexes described in U.S. Pat. No. 4,889,647. The complexes are reaction products of a fatty oil, dithanolamine and a molybdenum source. Specific chemical structures have not been assigned to the complexes. U.S. Pat. No. 4,889,647 reports an infrared spectrum for a typical reaction product of that disclosure; the spectrum identifies an ester carbonyl band at 1740 $cm^{-1}$ and an amide carbonyl band at 1620 $cm^{-1}$. The fatty oils are glyceryl esters of higher fatty acids containing at least 12 carbon atoms up to 22 carbon atoms or more. The molybdenum source is an oxygen-containing compound such as ammonium molybdates, molybdenum oxides and mixtures.

Other organo molybdenum complexes which can be used in the present disclosure are tri-nuclear molybdenum-sulfur compounds described in EP 1 040 115 and WO 99/31113 and the molybdenum complexes described in U.S. Pat. No. 4,978,464

Performance and Uses

The lubricant compositions of this disclosure give advantaged performance in the lubrication of internal combustion engines, power trains, drivelines, transmissions, gears, gear trains, gear sets, compressors, pumps, hydraulic systems, bearings, bushings, turbines, and the like, Also, the lubricant compositions of this disclosure give advantaged friction, wear, and other lubricant performances in the lubrication of mechanical components, which comprise, for example, pistons, piston rings, cylinder liners, cylinders, cams, tappets, lifters, bearings (journal, roller, tapered, needle, ball, and the like), gears, valves, and the like.

Further, the lubricant compositions of this disclosure give advantaged friction, wear, and other lubricant performances under a range of lubrication contact pressures, from 1 MPa to greater than 10 GPa, preferably greater than 10 MPa, more preferably greater that 100 MPa, even more preferable greater than 300 MPa. Under certain circumstances, the instant disclosure gives advantaged wear and friction performance at greater than 0.5 GPa, often at greater than 1 GPa, sometimes greater than 2 GPa, under selected circumstances greater than 5 GPa.

Yet further, the lubricant compositions of this disclosure give advantaged friction, wear, and other lubricant performances when used in combination with lubricated surfaces comprising: metals, metal alloys, non-metals, non-metal alloys, mixed carbon-metal composites and alloys, mixed carbon-nonmetal composites and alloys, ferrous metals, ferrous composites and alloys, non-ferrous metals, non-ferrous composites and alloys, titanium, titanium composites and alloys, aluminum, aluminum composites and alloys, magnesium, magnesium composites and alloys, ion-implanted metals and alloys, plasma modified surfaces; surface modified materials; coatings; mono-layer, multi-layer, and gradient layered coatings; honed surfaces; polished surfaces; etched surfaces; textured surfaces; micro and nano structures on textured surfaces; super-finished surfaces; diamond-like carbon (DLC), DLC with high-hydrogen content, DLC with moderate hydrogen content, DLC with low-hydrogen content, DLC with zero hydrogen content, DLC composites, DLC-metal compositions and composites, DLC-nonmetal compositions and composites; glasses, metallic glasses; ceramics, cermets, ceramic oxides, ceramic nitrides, FeN, CrN, ceramic carbides, mixed ceramic compositions, and the like; polymers, plastics, thermoplastic polymers, engineered polymers, polymer blends, polymer alloys, polymer composites; elastomers; materials compositions and composites containing dry lubricants, comprising for example graphite, carbon, molybdenum, molybdenum disulfide, polytetrafluoroethylene, polyperfluoropropylene, polyperfluoroalkylethers, and the like.

The viscometric properties of the lubricants of this disclosure can be measured according to standard practices. A low viscosity can be advantageous for lubricants in modern equipment. A low high temperature high shear (HTHS) viscosity, in accordance with ASTM D4683, can indicate performance of a lubricant in a modern engine. In particular, the lubricants of this disclosure can have an HTHS of less than 2.0 cP, or more preferably less than 1.9 cP, or more preferably less than 1.8 cP, or more preferably less than 1.7 cP.

The lubricants of this disclosure can have lower volatility, as determined by the Noack volatility test ASTM D5800, or as predicted by a TGA test that simulates the Noack volatility. In particular, the lubricants of this disclosure can have a Noack between 1% and 50%, or more preferably between 2% and 40%, or more preferably between 3% and 30%, or more preferably between 4% and 25%. Particularly preferred compositions have a Noack below 25%.

The lubricants of this disclosure can have reduced traction as determined by the MTM (Mini Traction Machine) traction test. Traction is most easily assessed by comparison to a reference fluid, in this case a suitable reference fluid is an engine oil formulated with commercial dioctyl adipate ester such as Esterex™ A32. Accordingly, the lubricants of this disclosure can have an MTM traction reduction of 5% versus a reference, or more preferably a reduction of 10% versus a reference, or more preferably a reduction of 20% versus a reference, or more preferably a reduction of 30% versus a reference, or more preferably a reduction of 40% versus a reference.

In the above detailed description, the specific embodiments of this disclosure have been described in connection with its preferred embodiments. However, to the extent that the above description is specific to a particular embodiment or a particular use of this disclosure, this is intended to be illustrative only and merely provides a concise description of the exemplary embodiments. Accordingly, the disclosure is not limited to the specific embodiments described above, but rather, the disclosure includes all alternatives, modifications, and equivalents falling within the true scope of the appended claims. Various modifications and variations of this disclosure will be obvious to a worker skilled in the art and it is to be understood that such modifications and variations are to be included within the purview of this application and the spirit and scope of the claims.

EXAMPLES

Example 1

Preparation of Dihexyl 2-octylsuccinate diester

To a 2-neck 1000-ml round-bottomed flask was added n-octylsuccinic anhydride (120 g, 565.26 mmol, 1.0 equiv.), 1-hexanol (173.26 g, 1695.8 mmol, 3.00 equiv.), toluene (150 ml) and p-toluenesulfonic acid monohydrate (1.0752 g, 5.652 mmol, 0.010 equiv.) at room temperature. The resulting mixture was heated at reflux with stirring in an oil bath at 136° C. under a nitrogen atmosphere for 17 hours. The water produced in the reaction was collected in a Dean-Stark trap. The cooled mixture was diluted with hexanes, washed with dilute aqueous $Na_2CO_3$ solution, water, brine, dried ($MgSO_4$), filtered, and concentrated in vacuo to afford a crude product. Excess solvent was further removed by heating the crude product with stirring in an oil bath under high vacuum for 4 hours to afford a clear liquid (217.2 g, 96%).

Example 2

Preparation of Diheptyl 2-octylsuccinate diester

To a 2-neck 500-ml round-bottomed flask was added n-octylsuccinic anhydride (110 g, 518.16 mmol, 1.0 equiv.), 1-heptanol (180.63 g, 1554.5 mmol, 3.00 equiv.), toluene (175 ml) and p-toluenesulfonic acid monohydrate (0.9856 g, 5.1819 mmol, 0.010 equiv.) at room temperature. The resulting mixture was heated at reflux with stirring in an oil bath at 138° C. under a nitrogen atmosphere for 18 hours. The water produced in the reaction was collected in a Dean-Stark trap. The cooled mixture was diluted with hexanes, washed with dilute aqueous $Na_2CO_3$ solution, water, brine, dried ($MgSO_4$), filtered, and concentrated in vacuo to afford a crude product. Excess solvent was further removed by heating the crude product with stirring in an oil bath under high vacuum for 3 hours to afford a clear liquid (206.1 g, 93%).

Example 3

Preparation of Dipentyl 2-dodecylsuccinate diester

To a 2-neck 1000-ml round-bottomed flask was added n-dodecylsuccinic anhydride (100 g, 372.59 mmol, 1.0 equiv.), 1-pentanol (131.38 g, 1490.4 mmol, 4.00 equiv.), toluene (200 ml) and p-toluenesulfonic acid monohydrate (0.7087 g, 3.7257 mmol, 0.010 equiv.) at room temperature. The resulting mixture was heated at reflux with stirring in an oil bath at 132° C. under a nitrogen atmosphere for 25 hours. The resulting mixture was heated at reflux with stirring in an oil bath at 138° C. under a nitrogen atmosphere for 18 hours. The water produced in the reaction was collected in a Dean-Stark trap. The cooled mixture was diluted with hexanes, washed with dilute aqueous $Na_2CO_3$ solution, water, brine, dried ($MgSO_4$), filtered, and concentrated in vacuo to afford a crude product. Excess solvent was further removed by heating the crude product with stirring in an oil bath under high vacuum for 4 hours to afford a clear liquid (150.8 g, 95%).

Example 4

Lube Properties

The lube properties of the products of Examples 1-3 were evaluated and the data are shown in FIGS. 1 and 2. The kinematic viscosity (Kv) of the liquid product was measured using ASTM D445 and D7042, and reported at temperatures of 100° C. (Kv at 100° C.) or 40° C. (Kv at 40° C.). The viscosity index (VI) was measured according to ASTM D2270 using the measured kinematic viscosities for each product. Noack volatility was determined by ASTM D5800. These fluids were evaluated as Group V base stocks and the results are shown in FIGS. 1 and 2.

FIGS. 1 and 2 clearly show that the diester base stock examples of this disclosure (Examples 1-3) all have more desirable viscosity-volatility properties when compared to the commercially available low viscosity ester base stocks from different sources. In particular, the diester base stocks of this disclosure have lower viscosities than commercially available esters at similar volatility (e.g., compare Examples 2 and 3 with entries 7, 8 and 13 in FIG. 1). Also, the diester base stocks of this disclosure have lower volatility than commercially available esters at comparable viscosities (e.g., compare Example 2 with entries 4 and 11 in FIG. 1).

FIG. 2 is a plot of kinematic viscosity (100° C.)) versus volatility (Noack) for selected examples of this disclosure (Examples 1-3 as filled circles) and commercially available ester base stocks (entries 4-13 as filled triangles) based on data in FIG. 1. The desirable examples of this disclosure have their volatility defined by the formula: Noack volatility (D5800) is not greater than Noack=$[-18 (Kv_{100})+70]$.

Example 5

Lube Properties

Selected diester base stocks of this disclosure (i.e., Example 1 and Example 2) and commercial base stocks were used to formulate ultra-low viscosity engine oils. Each formulation consisted of 82.3% by weight of the base stock and 17.7% by weight of an additive package. The additive package employed is composed of commonly used additive components (e.g., antiwear additives, friction modifiers, dispersants, detergents, antioxidants, pour point depressants, antifoaming agent, etc.). These diester base stocks exhibit high solvency for the additive components. Potential higher viscosity engine oil grade can be formulated by addition of viscosity modifiers.

High temperature high shear (HTHS) viscosity and Noack volatility results for low-viscosity engine oils formulated with base stocks of this disclosure are shown in FIG. 3. The HTHS test was conducted in accordance with ASTM D4683. Noack volatility was determined by ASTM D5800.

By comparing formulations prepared from the base stocks of Example 1 and Example 2 with those prepared from commercially available low-viscosity base stocks (i.e., entries 3-5), it is clear that the diester base stocks of this disclosure show lower HTHS viscosity, lower volatility, and better additives compatibility than commercial polyol esters (i.e., entries 4 and 5), and substantially improved viscosity/volatility performance versus entry 3 (i.e., a commercial widely used diester.

Figure 4:
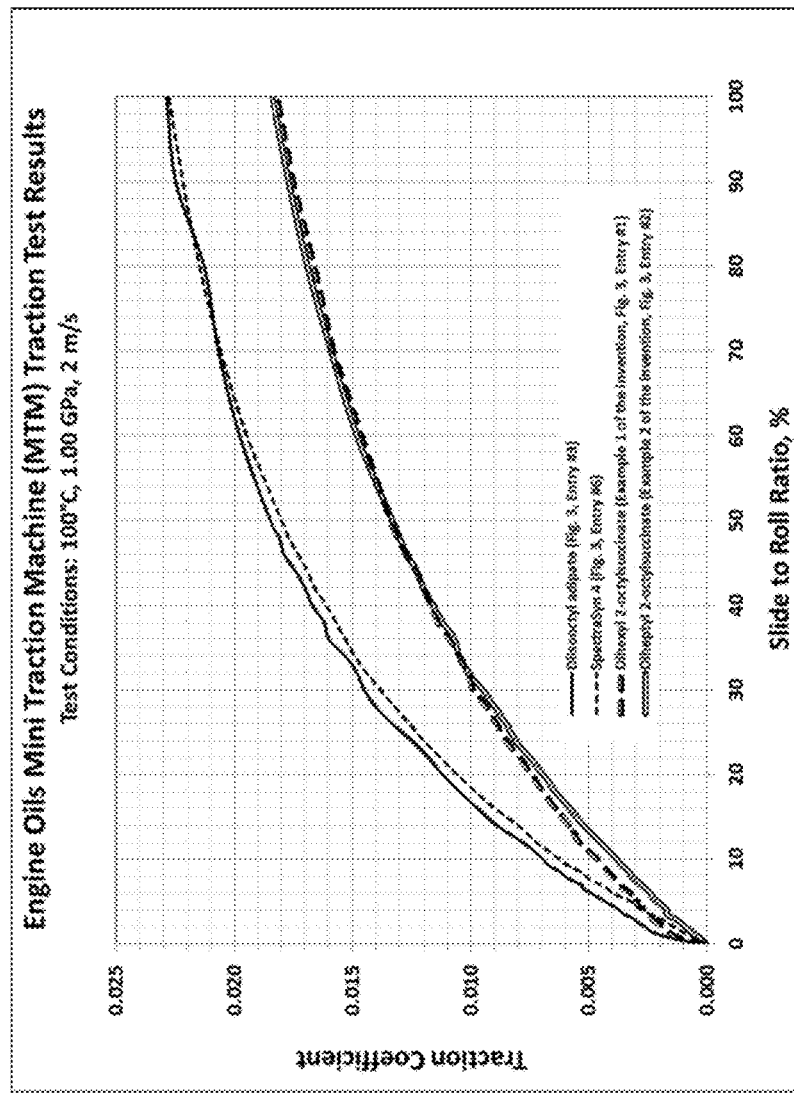
FIG. 4 shows MTM-traction curves from selected diester fluids of this disclosure and commercial esters in MTM (mini-traction machine) traction test at 100° C. and 1.00 GPa in accordance with Example 5.

Frictional characteristics of selected ester fluids of this disclosure were assessed using the MTM (Mini Traction Machine) traction test. In this test, the fluids were subjected to high pressure and high temperature when a stainless steel highly polished ball under high load was moved against a plate, both submerged into the fluids at the test temperature. The test started with the ball rolling at 100% then gradually sliding to a pure 100% sliding mode at the end of test. The traction of coefficient is an indication of the energy lost due to the fluids shearing. More energy efficient fluids have lower traction coefficients. FIG. 4 shows graphically MTM traction curves from the diester fluids of Example 1 and Example 2 and two commercial fluids in MTM (mini-traction machine) Traction test at 100° C. and 1.00 GPa). In addition, formulations using Examples 1 and 2 show outstanding traction characteristics when compared to the commercial diester and Group IV PAO, as indicated by the calculated average traction coefficients measured using an MTM (mini Traction Machine) at 100° C., 1 GPa and 0-100% SRR and displayed in FIG. 3.

As shown in FIG. 3 and FIG. 4, the diester fluids of this disclosure exhibited better energy efficiency than the commercially available esters as indicated by close to 30% lower average traction coefficients.

Oxidative stability of Example 2 of this disclosure was assessed using 2 oxidation tests: The Catalytic Oxidation Test at 325° F. (163° C.) and 120 hours and the 210 Hour Oxidation Stability Test at 165° C. The Catalytic Oxidation test consists basically of bubbling a stream of air through a volume of the lubricant at the rate of five liters per hour at 325° F. See U.S. Pat. No. 3,682,980 which is incorporated herein by reference. The 210 Hour Oxidation Stability Test consists basically in placing the lubricant in a heated oxidation cell in presence of 50 ppm Fe acetoacetate catalyst and heated air bubbling with a periodical sampling to measure the kinematic viscosity at 40° C. See U.S. Pat. No. 8,569,216 which is incorporated herein by reference.

As shown in FIG. 5, the diester of this disclosure exhibited better oxidative stability than the commercially available diester as indicated by the low increase in Kv100 viscosity (9.4% vs. 34.5%) in the Catalytic Oxidation Test and the more than 210 hours to reach the 200% Kv40 increase limit in the 210 Oxidation Stability Test (>210 hours vs. 97 hours). The diester of this disclosure also outperforms the Group IV PAO formulation.

PCT and EP Clauses:

1. A composition comprising one or more compounds represented by the formula

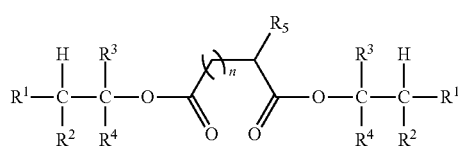

wherein each $R_1$ is independently a substituted or unsubstituted linear alkyl group ($C_1$-$C_{30}$), each $R_2$, $R_3$ and $R_4$ is hydrogen, $R_5$ is a substituted or unsubstituted alkyl group ($C_8$-$C_{30}$) or alkenyl group ($C_8$-$C_{30}$), and n is a value from 0 to 7; wherein said composition has a viscosity ($Kv_{100}$) from 1 cSt to 10 cSt at 100° C. as determined by ASTM D445, a viscosity index (VI) from −100 to 300 as determined by ASTM D2270, and a Noack volatility of no greater than 50 percent as determined by ASTM D5800.

2. The composition of clause 1 wherein the Noack volatility as determined by ASTM D5800 is not greater than Noack=[−18($Kv_{100}$)+70].

3. The composition of clauses 1 and 2 wherein each $R_1$ is independently a substituted or unsubstituted linear alkyl group ($C_1$-$C_{20}$), each $R_2$, $R_3$ and $R_4$ is hydrogen, $R_5$ is a substituted or unsubstituted alkyl group ($C_8$-$C_{20}$) or alkenyl group ($C_8$-$C_{20}$), and n is a value from 0 to 6.

4. The composition of clauses 1-3 wherein each $R_1$ is independently a substituted or unsubstituted linear alkyl group ($C_1$-$C_{10}$), each $R_2$, $R_3$ and $R_4$ is hydrogen, $R_5$ is a substituted or unsubstituted alkyl group ($C_8$-$C_{10}$) or alkenyl group ($C_8$-$C_{10}$), and n is a value from 0 to 5.

5. The composition of clauses 1-4 which is selected from the group consisting of dihexyl 2-octylsuccinate, diheptyl 2-octylsuccinate, and dipentyl 2-dodecylsuccinate.

6. The composition of clauses 1-5 which has a high temperature high shear (HTHS) viscosity of less than 1.7 cP as determined by ASTM D4683, and a Noack volatility from 10 to 30 percent as determined by ASTM D5800.

7. A composition comprising one or more compounds represented by the formula

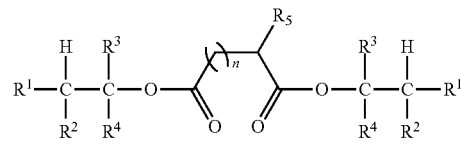

wherein each $R_1$ is independently a substituted or unsubstituted linear alkyl group ($C_1$-$C_{30}$), each $R_2$, $R_3$ and $R_4$ is hydrogen, $R_5$ is a substituted or unsubstituted alkyl group ($C_8$-$C_{30}$) or alkenyl group ($C_8$-$C_{30}$), and n is a value from 0 to 7; wherein said composition has a viscosity ($Kv_{100}$) from 1 cSt to 10 cSt at 100° C. as determined by ASTM D445, a viscosity index (VI) from −100 to 300 as determined by ASTM D2270, and a Noack volatility of no greater than 50 percent as determined by ASTM D5800; wherein said one or more compounds are produced by a process comprising reacting a substituted or unsubstituted alcohol having a hydrogen attached to a beta carbon thereof with a substituted or unsubstituted carboxylic diacid or anhydride, optionally in the presence of a catalyst and a solvent, under reaction conditions sufficient to produce said one or more compounds.

8. A lubricating oil base stock comprising one or more compounds represented by the formula

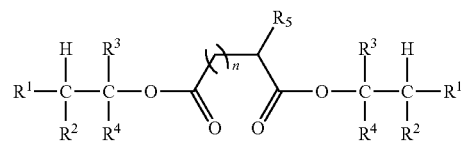

wherein each $R_1$ is independently a substituted or unsubstituted linear alkyl group ($C_1$-$C_{30}$), each $R_2$, $R_3$ and $R_4$ is hydrogen, $R_5$ is a substituted or unsubstituted alkyl group ($C_8$-$C_{30}$) or alkenyl group ($C_8$-$C_{30}$), and n is a value from 0 to 7; wherein said composition has a viscosity ($Kv_{100}$) from 1 cSt to 10 cSt at 100° C. as determined by ASTM D445, a viscosity index (VI) from −100 to 300 as determined by ASTM D2270, and a Noack volatility of no greater than 50 percent as determined by ASTM D5800.

9. The lubricating oil base stock of clause 8 wherein each $R_1$ is independently a substituted or unsubstituted linear alkyl group ($C_1$-$C_{20}$), each $R_2$, $R_3$ and $R_4$ is hydrogen, $R_5$ is a substituted or unsubstituted alkyl group ($C_8$-$C_{20}$) or alkenyl group ($C_8$-$C_{20}$), and n is a value from 0 to 6.

10. The lubricating oil base stock of clauses 8 and 9 wherein each $R_1$ is independently a substituted or unsubstituted linear alkyl group ($C_1$-$C_{10}$), each $R_2$, $R_3$ and $R_4$ is hydrogen, $R_5$ is a substituted or unsubstituted alkyl group ($C_8$-$C_{10}$) or alkenyl group ($C_8$-$C_{10}$), and n is a value from 0 to 7.

11. The lubricating oil base stock of clauses 8-10 which is selected from the group consisting of dihexyl 2-octylsuccinate, diheptyl 2-octylsuccinate, and dipentyl 2-dodecylsuccinate.

12. The lubricating oil base stock of clauses 8-11 which has a high temperature high shear (HTHS) viscosity of less than 1.7 cP as determined by ASTM D4683, and a Noack volatility from 10 to 30 percent as determined by ASTM D5800.

13. A lubricating oil comprising a lubricating oil base stock component, and a diester cobase stock component; wherein said diester cobase stock comprises one or more compounds represented by the formula

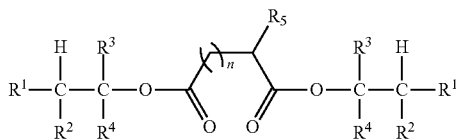

wherein each $R_1$ is independently a substituted or unsubstituted linear alkyl group ($C_1$-$C_{30}$), each $R_2$, $R_3$ and $R_4$ is hydrogen, $R_5$ is a substituted or unsubstituted alkyl group ($C_8$-$C_{30}$) or alkenyl group ($C_8$-$C_{30}$), and n is a value from 0 to 7; wherein said composition has a viscosity ($Kv_{100}$) from 1 cSt to 10 cSt at 100° C. as determined by ASTM D445, a viscosity index (VI) from −100 to 300 as determined by ASTM D2270, and a Noack volatility of no greater than 50 percent as determined by ASTM D5800.

14. The lubricating oil of clause 13 further comprising one or more of a viscosity improver, antioxidant, detergent, dispersant, pour point depressant, corrosion inhibitor, metal deactivator, seal compatibility additive, anti-foam agent, inhibitor, and anti-rust additive.

15. A method for improving one or more of oxidative stability, solubility and dispersancy of polar additives of a lubricating oil by using as the lubricating oil a formulated oil comprising a lubricating oil base stock as a major component, and a diester cobase stock as a minor component; wherein said diester cobase stock comprises one or more compounds represented by the formula

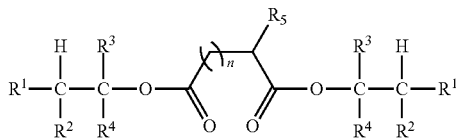

wherein each $R_1$ is independently a substituted or unsubstituted linear alkyl group ($C_1$-$C_{30}$), each $R_2$, $R_3$ and $R_4$ is hydrogen, $R_5$ is a substituted or unsubstituted alkyl group ($C_8$-$C_{30}$) or alkenyl group ($C_8$-$C_{30}$), and n is a value from 0 to 7; wherein said composition has a viscosity ($Kv_{100}$) from 1 cSt to 10 cSt at 100° C. as determined by ASTM D445, a viscosity index (VI) from −100 to 300 as determined by ASTM D2270, and a Noack volatility of no greater than 50 percent as determined by ASTM D5800.

All patents and patent applications, test procedures (such as ASTM methods, UL methods, and the like), and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

The invention claimed is:

1. A composition comprising one or more compounds selected from the group consisting of dihexyl 2-octyladipate, diheptyl 2-octyladipate, and dipentyl 2-dodecyladipate; wherein said composition has a viscosity ($Kv_{100}$) from about 1 cSt to about 10 cSt at 100° C. as determined by ASTM D445, a viscosity index (VI) from about −100 to about 300 as determined by ASTM D2270, and a Noack volatility of no greater than 50 percent as determined by ASTM D5800.

2. The composition of claim 1 wherein the Noack volatility as determined by ASTM D5800 is not greater than Noack=[−18($Kv_{100}$)+70].

3. The composition of claim 1 which has a high temperature high shear (HTHS) viscosity of less than about 1.7 cP as determined by ASTM D4683, and a Noack volatility from about 10 to about 30 percent as determined by ASTM D5800.

4. The composition of claim 1 which has a high temperature high shear (HTHS) viscosity of less than about 1.6 cP as determined by ASTM D4683, and a Noack volatility from about 12 to about 28 percent as determined by ASTM D5800.

5. The composition of claim 1 which has a viscosity ($Kv_{100}$) from about 2 cSt to about 8 cSt at 100° C. as determined by ASTM D445, a viscosity index (VI) from about 25 to about 150 as determined by ASTM D2270, and a Noack volatility of no greater than 25 percent as determined by ASTM D5800.

6. A composition comprising one or more compounds selected from the group consisting of dihexyl 2-octyladipate, diheptyl 2-octyladipate, and dipentyl 2-dodecyladipate;

wherein said composition has a viscosity ($Kv_{100}$) from about 1 cSt to about 10 cSt at 100° C. as determined by ASTM D445, a viscosity index (VI) from about −100 to about 300 as determined by ASTM D2270, and a Noack volatility of no greater than 50 percent as determined by ASTM D5800; wherein said one or more compounds are produced by a process comprising reacting a substituted or unsubstituted alcohol having a hydrogen attached to a beta carbon thereof with a substituted or unsubstituted carboxylic diacid or anhydride, optionally in the presence of a catalyst and a solvent, under reaction conditions sufficient to produce said one or more compounds.

7. A lubricating oil base stock comprising one or more compounds selected from the group consisting of dihexyl 2-octyladipate, diheptyl 2-octyladipate, and dipentyl 2-dodecyladipate;
wherein said composition has a viscosity ($Kv_{100}$) from about 1 cSt to about 10 cSt at 100° C. as determined by ASTM D445, a viscosity index (VI) from about −100 to about 300 as determined by ASTM D2270, and a Noack volatility of no greater than 50 percent as determined by ASTM D5800.

8. The lubricating oil base stock of claim 7 which has a high temperature high shear (HTHS) viscosity of less than about 1.7 cP as determined by ASTM D4683, and a Noack volatility from about 10 to about 30 percent as determined by ASTM D5800.

9. The lubricating oil base stock of claim 7 which has a high temperature high shear (HTHS) viscosity of less than about 1.6 cP as determined by ASTM D4683, and a Noack volatility from about 12 to about 28 percent as determined by ASTM D5800.

10. The lubricating oil base stock of claim 7 which has a viscosity ($Kv_{100}$) from about 2 cSt to about 8 cSt at 100° C. as determined by ASTM D445, a viscosity index (VI) from about 25 to about 150 as determined by ASTM D2270, and a Noack volatility of no greater than 25 percent as determined by ASTM D5800.

11. The lubricating oil base stock of claim 7 further comprising one or more of a viscosity improver, antioxidant, detergent, dispersant, pour point depressant, corrosion inhibitor, metal deactivator, seal compatibility additive, anti-foam agent, inhibitor, and anti-rust additive.

12. A lubricating oil comprising a lubricating oil base stock component, and a diester cobase stock component; wherein said diester cobase stock comprises one or more compounds selected from the group consisting of dihexyl 2-octyladipate, diheptyl 2-octyladipate, and dipentyl 2-dodecyladipate;
wherein said composition has a viscosity ($Kv_{100}$) from about 1 cSt to about 10 cSt at 100° C. as determined by ASTM D445, a viscosity index (VI) from about −100 to about 300 as determined by ASTM D2270, and a Noack volatility of no greater than 50 percent as determined by ASTM D5800.

13. The lubricating oil of claim 12 wherein the lubricating oil base stock comprises a Group I, II, III, IV or V base oil stock.

14. The lubricating oil of claim 12 wherein the lubricating oil base stock comprises a polyalphaolefin (PAO) or gas-to-liquid (GTL) oil base stock.

15. The lubricating oil of claim 12 wherein the lubricating oil base stock is present in an amount from about 1 weight percent to about 99 weight percent, and the diester cobase stock is present in an amount from about 1 weight percent to about 99 weight percent, based on the total weight of the lubricating oil.

16. The lubricating oil of claim 12 which has a high temperature high shear (HTHS) viscosity of less than about 1.7 cP as determined by ASTM D4683, and a Noack volatility from about 10 to about 30 percent as determined by ASTM D5800.

17. The lubricating oil of claim 12 which has a high temperature high shear (HTHS) viscosity of less than about 1.6 cP as determined by ASTM D4683, and a Noack volatility from about 12 to about 28 percent as determined by ASTM D5800.

18. The lubricating oil of claim 12 which has a viscosity ($Kv_{100}$) from about 2 cSt to about 8 cSt at 100° C. as determined by ASTM D445, a viscosity index (VI) from about 25 to about 150 as determined by ASTM D2270, and a Noack volatility of no greater than 25 percent as determined by ASTM D5800.

19. The lubricating oil of claim 12 further comprising one or more of a viscosity improver, antioxidant, detergent, dispersant, pour point depressant, corrosion inhibitor, metal deactivator, seal compatibility additive, anti-foam agent, inhibitor, and anti-rust additive.

20. A method for improving one or more of oxidative stability, solubility and dispersancy of polar additives of a lubricating oil comprising:
providing a lubricating oil comprising a lubricating oil base stock as a major component, and a diester cobase stock as a minor component; wherein said diester cobase stock comprises one or more compounds selected from the group consisting of dihexyl 2-octyladipate, diheptyl 2-octyladipate, and dipentyl 2-dodecyladipate;
wherein said composition has a viscosity ($Kv_{100}$) from about 1 cSt to about 10 cSt at 100° C. as determined by ASTM D445, a viscosity index (VI) from about −100 to about 300 as determined by ASTM D2270, and a Noack volatility of no greater than 50 percent as determined by ASTM D5800, and
using the lubricating oil to lubricate a mechanical component selected from the group consisting of pistons, piston rings, cylinder liners, cylinders, cams, tappets, lifters, bearings, gears, and valves to improve one or more of oxidative stability, solubility and dispersancy of polar additives in the lubricating oil.

21. The method of claim 20 wherein the lubricating oil base stock comprises a Group I, II, III, IV or V base oil stock.

22. The method of claim 20 wherein the lubricating oil base stock comprises a polyalphaolefin (PAO) or gas-to-liquid (GTL) oil base stock.

23. The method of claim 20 wherein the lubricating oil base stock is present in an amount from about 1 weight percent to about 99 weight percent, and the diester cobase stock is present in an amount from about 1 weight percent to about 99 weight percent, based on the total weight of the lubricating oil.

24. The method of claim 20 wherein the lubricating oil has a high temperature high shear (HTHS) viscosity of less than about 1.7 cP as determined by ASTM D4683, and a Noack volatility from about 10 to about 30 percent as determined by ASTM D5800.

25. The method of claim 20 wherein the lubricating oil has a high temperature high shear (HTHS) viscosity of less than about 1.6 cP as determined by ASTM D4683, and a Noack volatility from about 12 to about 28 percent as determined by ASTM D5800.

26. The method of claim 20 wherein the lubricating oil has a viscosity ($Kv_{100}$) from about 2 cSt to about 8 cSt at 100° C. as determined by ASTM D445, a viscosity index (VI) from about 25 to about 150 as determined by ASTM D2270, and a Noack volatility of no greater than 25 percent as determined by ASTM D5800.

27. The method of claim 20 wherein the lubricating oil further comprises one or more of a viscosity improver, antioxidant, detergent, dispersant, pour point depressant, corrosion inhibitor, metal deactivator, seal compatibility additive, anti-foam agent, inhibitor, and anti-rust additive.

28. The method of claim 20 wherein the lubricating oil has a MTM traction reduction of 5% versus diioctyl adipate ester as determined by the MTM (Mini Traction Machine) traction test.

* * * * *